US009458516B2

(12) United States Patent
Aida et al.

(10) Patent No.: US 9,458,516 B2
(45) Date of Patent: Oct. 4, 2016

(54) KIT FOR DETECTING BOVINE LEUKEMIA VIRUS(BLV), AND USE THEREOF

(75) Inventors: Yoko Aida, Wako (JP); Shin-nosuke Takeshima, Wako (JP); Mayuko Jimba, Wako (JP); Daiji Endoh, Wako (JP)

(73) Assignee: RIKEN, Wako-shi, Saitama (JP)

( * ) Notice: Subject to any disclaimer, the term of this patent is extended or adjusted under 35 U.S.C. 154(b) by 445 days.

(21) Appl. No.: 13/879,243

(22) PCT Filed: Oct. 21, 2011

(86) PCT No.: PCT/JP2011/074887
§ 371 (c)(1),
(2), (4) Date: Jun. 14, 2013

(87) PCT Pub. No.: WO2012/053666
PCT Pub. Date: Apr. 26, 2012

(65) Prior Publication Data
US 2014/0147834 A1    May 29, 2014

Related U.S. Application Data

(60) Provisional application No. 61/405,433, filed on Oct. 21, 2010.

(51) Int. Cl.
*C12Q 1/68* (2006.01)
*C12P 19/34* (2006.01)
*C07H 21/04* (2006.01)
*C12Q 1/70* (2006.01)

(52) U.S. Cl.
CPC ..................... *C12Q 1/701* (2013.01)

(58) Field of Classification Search
USPC .............. 435/6.12, 91.2, 810; 536/24.33
See application file for complete search history.

(56) References Cited

U.S. PATENT DOCUMENTS 5,210,015 A * 5/1993 Gelfand et al. .............. 435/6.11

FOREIGN PATENT DOCUMENTS

WO        2010/036134        4/2010

OTHER PUBLICATIONS

Lowe et al. (Nucleic acid research, 1990, vol. 18(7), p. 1757-1761.*
Zhao et al. (ScienceDirect, 2007, vol. 124. p. 113-124).*
Nucleic acid sequence search reports:AC:DQ288231 & DQ288223.*
Lloyd-Smith, James O. et al, "Epidemic dynamics at the human-animal interface" Science 2009, vol. 326, pp. 1362-1367.
Tapper, M. L , "Emerging viral diseases and infectious disease risks", Haemophilia 2006, 12 Suppl 1, pp. 3-7.
Endoh, D. et al, "Species-independent detection of RNA virus by representational difference analysis using non-ribosomal hexanucleotides for reverse transcription" Nucleic Acids Research 2005, vol. 33, No. 6 e65, pp. 1-11.
Rose, Timothy M. et al, "Consensus-degenerate hybrid oligonucleotide primers for amplification of distantly related sequences" Nucleic Acids Research 1998, vol. 26, No. 7, pp. 1628-1635.
Bartl, S. "Amplification using degenerate primers with multiple inosines to isolate genes with minimal sequence similarity", Methods in Molecular Biology, 1997, vol. 67, 451-457.
Moonka, D. et al, "A consensus primer to amplify both alpha and beta chains of the human T cell receptor", Journal of Immunological Methods 1994, 169, pp. 41-51.
Rose, Timothy M. et al, "CODEHOP (COnsensus-DE generate Hybrid Oligonucleotide Primer) PCR primer design", Nucleic Acids Research 2003, vol. 31, No. 13, pp. 3763-3766.
Katoh, K. et al, "Recent developments in the MAFFT multiple sequence alignment program" Briefing in Bioinformatics. 2008, vol. 9, No. 4. pp. 286-298.
Gillet, N. et al, "Mechanisms of leukemogenesis induced by bovine leukemia virus: prospects for novel anti-retroviral therapies in human", Retrovirology 2007, 4:18, pp. 1-32.
Alexandersen, S. et al, "Identification of alternatively spliced mRNAs encoding potential new regulatory proteins in cattle infected with bovine leukemia virus", Journal of Virology, Jan. 1993, vol. 67, No. 1, pp. 39-52.
Kettmann, R. et al, "Integration of bovine leukemia virus DNA in the bovine genome", Proc Natl Acad Sci U S A Oct. 1979, vol. 76, pp. 4822-4826.
Kettmann, R. et al, "Leukemogenesis by bovine leukemia virus: proviral DNA integration and lack of RNA expression of viral long terminal repeat and 3' proximate cellular sequences", Proc Natl Acad Sci U S A Apr. 1982, vol. 79, pp. 2465-2469.
Kettmann, R. et al, "Genomic integration of bovine leukemia provirus: comparison of persistent lymphocytosis with lymph node tumor form of enzootic bovine leucosis", Proc Natl Acad Sci U S A, May 1980, vol. 77, pp. 2577-2581.
Lagarias, D. M. et al, "Transcriptional activation of bovine leukemia virus in blood cells from experimentally infected, asymptomatic sheep with latent infections", Journal of Virology, May 1989, vol. 63, pp. 2099-2107.
Aida, Y. et al, "Further phenotypic characterization of target cells for bovine leukemia virus experimental infection in sheep", Am J Vet Res 1989, vol. 50, pp. 1946-1951.
Wang, Chung-Tshen "Bovine leukemia virus infection in Taiwan: epidemiological study", J Vet Med Sci 1991, 53, pp. 395-398.
Monti, G. E. et al, "Evaluation of a new antibody-based enzyme-linked immunosorbent assay for the detection of bovine leukemia virus infection in dairy cattle", J Vet Diagn Invest 2005, 17, pp. 451-457.

(Continued)

*Primary Examiner* — Kenneth R. Horlick
*Assistant Examiner* — Joyce Tung
(74) *Attorney, Agent, or Firm* — Casimir Jones, SC

(57) ABSTRACT

A kit for detecting Bovine leukemia virus (BLV) according to the present invention includes: a first PCR primer being oligonucleotide including successive 20 bases or more in the base sequence denoted by SEQ ID NO: 1, the first PCR primer being oligonucleotide having 50 bases or less; and second PCR primer being including successive 20 bases or more in the base sequence denoted by SEQ ID NO: 2, the second PCR primer being oligonucleotide having 50 bases or less is included.

9 Claims, 9 Drawing Sheets

(56) References Cited

OTHER PUBLICATIONS

Kurdi, A. et al, "Serologic and virologic investigations on the presence of BLV infection in a dairy herd in Syria", Study on the presence of BLV infection in a dairy herd in Syria by using serological and virological tests, Berl Munch Tierarztl Wochenschr 1999, 112, pp. 18-23.

Zaghawa, A. et al, "An outbreak of enzootic bovine leukosis in upper Egypt: clinical, laboratory and molecular-epidemiological studies", J Vet Med B 49, 2002, pp. 123-129.

Schoepf, K. C. et al, "Serological evidence of the occurrence of enzootic bovine leukosis (EBL) virus infection in cattle in Tanzania", Trop Anim Health Prod 1997, 29, pp. 15-19.

Tajima, S. et al, "The region between amino acids 245 and 265 of the bovine leukemia virus (BLV) tax protein restricts transactivation not only via the BLV enhancer but also via other retrovirus enhancers", Journal of Virology, Dec. 2000, vol. 74, No. 23, pp. 10939-10949.

Tajima, S. et al, "A mutant form of the tax protein of bovine leukemia virus (BLV), with enhanced transactivation activity, increases expression and propagation of BLV in vitro but not in vivo", Journal of Virology, Feb. 2003, vol. 77, No. 3, pp. 1894-1903.

Tajima, S. et al, "Complete bovine leukemia virus (BLV) provirus is conserved in BLV-infected cattle throughout the course of B-cell lymphosarcoma development", Journal of Virology, Sep. 1998, vol. 72, No. 9, pp. 7569-7576.

Moratorio, G. et al, "Phylogenetic analysis of bovine leukemia viruses isolated in South America reveals diversification in seven distinct genotypes", Arch Virol 2010, 155, pp. 481-489.

Vanleeuewen, J. A. et al, "Seroprevalences of antibodies against bovine leukemia virus, bovine viral diarrhea virus, *Mycobacterium avium* subspecies paratuberculosis, and Neospora caninum in beef and dairy cattle in Manitoba", Can Vet J, Aug. 2006, vol. 47, pp. 783-786.

Kobayashi, S. et al, "Risk factors associated with within-herd transmission of bovine leukemia virus on dairy farms in Japan", BMC Veterinary Research, 2010, 6:1, pp. 1-6.

Rodriguez, S. M. et al, "Bovine leukemia virus can be classified into seven genotypes: evidence for the existence of two novel clades", Journal of General Virology 2009, 90, pp. 2788-2797.

Coulston, J. et al, "Molecular cloning and sequencing of an Australian isolate of proviral bovine leukaemia virus DNA: comparison with other isolates", Journal of Genral Virology, 1990, 71, pp. 1737-1746.

Asfaw, Y. et al, "Distribution and superinfection of bovine leukemia virus genotypes in Japan", Arch Virol 2005, 150, pp. 493-505.

Tong, S. et al, "Sensitive and broadly reactive reverse transcription-PCR assays to detect novel paramyxoviruses", Journal of Clinical Microbiology, Aug. 2008, vol. 46, No. 8, pp. 2652-2658.

Lew, A. et al, "Sensitive and specific detection of bovine immunodeficiency virus and bovine syncytial virus by 5' Taq nuclease assays with fluorescent 3' minor groove binder-DNA probes", Journal of Virological Methods 2004, 116, pp. 1-9.

Moens, B. et al, "Development and validation of a multiplex real-time PCR assay for simultaneous genotyping and human T-lymphotropic virus type 1, 2, and 3 proviral load determination", Journal of Clinical Microbiology, Nov. 2009, vol. 47, No. 11, pp. 3682-3691.

Dehee, A. et al, "Quantitation of HTLV-I proviral load by a TaqMan real-time PCR assay", Journal of Virological Methods 2002, 102, pp. 37-51.

Inabe, K. et al, "Transmission and propagation in cell culture of virus produced by cells transfected with an infectious molecular clone of bovine leukemia virus", Virology 1998, 245, pp. 53-64.

Aida, Y. et al, "Antigenic regions defined by monoclonal antibodies on tumor-associated antigens of bovine leukemia virus-induced lymphosarcoma cells", Leukmia Research, 1993, vol. 17, No. 2 pp. 187-193.

Aida, Y. et al, "Tumor-associated M(r) 34,000 and M(r) 32,000 membrane glycoproteins that are serine phosphorylated specifically in bovine leukemia virus-induced lymphosarcoma cells", Cancer Research, Dec. 1, 1992, 52, pp. 6463-6470.

Aida, Y. et al, "Phenotype and ontogeny of cells carrying a tumor-associated antigen that is expressed on bovine leukemia virus-induced lymphosarcoma", Cancer Research, Jan. 15, 1993, 53, pp. 429-437.

Aida, Y. et al, "Topographical analysis of tumor-associated antigens on bovine leukemia virus-induced bovine lymphosarcoma" Cancer Research, Mar. 1985, 45, pp. 1181-1186.

Aida, Y. et al, "The role of tumor-associated antigen in bovine leukemia virus-induced lymphosarcoma", Leukemia 1997, 11 Suppl 3, pp. 216-218.

Tajima, S. et al, "Function and conformation of wild-type p53 protein are influenced by mutations in bovine leukemia virus-induced B-cell lymphosarcoma", Virology 1998, 243, pp. 235-246.

Konnai, S. et al, "Tumor necrosis factor-alpha genetic polymorphism may contribute to progression of bovine leukemia virus-infection", Microbes and Infection 2006, 8, pp. 2163-2171.

Levy, D. et al, "Bovine leukemia virus specific antibodies among French cattle. I. Comparison of complement fixation and hematological tests", Int J Cancer 1977, 19, pp. 822-827.

Miyasaka, M. et al, Differentiation of B lymphocytes in sheep. II. Surface phenotype of B cells leaving the 'bursa-equivalent' lymphoid tissue of sheep, ileal Peyer's patches. Adv Exp Med Biol 1985, 186, pp. 119-126.

Onuma, M. et al, "Establishment of B-cell lines from tumor of enzootic bovine leucosis" Leukemia Research 1986, vol. 10, No. 6, pp. 689-695.

Hughes, S. H. et al, "Proviruses of avian sarcoma virus are terminally redundant, co-extensive with unintegrated linear DNA and integrated at many sites", Cell 1978, vol. 15, pp. 1397-1410.

Derse, D. et al, "Nucleotide sequence and structure of integrated bovine leukemia virus long terminal repeats", Virology 1985, 141, pp. 162-166.

Aida, Y. et al, "Cloning of cDNAs and the molecular evolution of a bovine MHC class II DRA gene", Biochemical and Biophysical Research Communications, 1994, vol. 204, No. 1, pp. 195-202.

Zhao, T. M. et al, "Characterization of an infectious molecular clone of human T-cell leukemia virus type I", Journal of Virology, Apr. 1995, vol. 69, No. 4, pp. 2024-2030.

Adachi, A. et al, "Production of acquired immunodeficiency syndrome-associated retrovirus in human and nonhuman cells transfected with an infectious molecular clone" Journal of Virology, Aug. 1986, vol. 59, No. 2, pp. 284-291.

Guan, Y. et al, "Construction and in vitro properties of a series of attenuated simian immunodeficiency viruses with all accessory genes deleted", Journal of Virology, May 2001, vol. 75, No. 9, pp. 4056-4067.

Yanagawa, S. et al, "Mouse mammary tumor virus with rearranged long terminal repeats causes murine lymphomas" Journal of Virology, Jan. 1993, vol. 67, No. 1, pp. 112-118.

Shackleford, G. M. et al, "Construction of a clonable, infectious, and tumorigenic mouse mammary tumor virus provirus and a derivative genetic vector", Proc Natl Acad Sci U S A Dec. 1988, vol. 85, pp. 9655-9659.

Jimba, M. et al., "Construction of real-time quantitative PCR method with use of condensed primer for quantifying bovine leukosis provirus and application thereof", The 147th Meeting of the Japanese Society of Veterinary Science Apr. 2-4, 2009, DP-31.

Endo, D et al., "Integrated research regarding establishment of viral hepatitis infection prevention system (H19-hepatitis-general-003)", Ministry of Health, Labour and Welfare Health Labour Sciences Research Grant (Research on Hepatitis and BSE) Summary / Cooperative Research Report, p. 5-49.

Endo, D et al., "Examination of highly reliable method of detecting virus with use of common primer between virus strains", Ministry of Health, Labour and Welfare Health Labour Sciences Research Grant (Research on Hepatitis and BSE)Cooperative Research Report Integrated research regarding establishment of viral hepatitis infection prevention system, p. 21-71.

Jimba, M. et al., "BLV-CoCoMo-qPCR: Quantitation of bovine leukemia virus proviral load using the CoCoMo algorithm", Retrovirology, (Nov. 2010), 7:91, pp. 1-19.

(56) References Cited

OTHER PUBLICATIONS

AU Patent Examination Report No. 1, AU Patent Application No. 2011318911, issued Aug. 19, 2014.

Kuckleburg, Christopher J., et al., "Detection of bovine leukemia virus in blood and milk by nested and real-time polymerase chain reactions," Journal of Veterinary Diagnostic Investigation, 2003, 15:72-76.

Marsolais, Gregoire, et al., "Importance of primer selection in the application of PCR technology to the diagnosis of bovine leukemia virus," Journal of Veterinary Diagnostic Investigation, 1994, 6:297-301.

European Search Report mailed Sep. 24, 2014, EP Patent Application No. 11834499.3.

Database Geneseq [Online], Sep. 30, 2010, "Viral family genomic sequence SEQ ID, No. 1209,", XP002729230, retrieved from EBI accession No. GSN:AYH01519, Database accession No. AYH01519.

Blakenstein, P., et al., "Polymerase Kettenreaktion (PCR) zum Nachweis von BLV-Provirus-praktikable Erganzung der BLV-Diagnostik?" Berliner Und Muenchener Tieraerztliche Wochenschrift, Paul Parey, Berlin, DE, vol. 111, No. 5, May 1, 1998, pp. 180-186, XP009176034.

Komiyama, Chiho, et al., "Development of loop-mediated isothermal amplification method for diagnosis of bovine leukemia virus infection," Journal of Virological Methods, Elsevier BV, NL, vol. 157, No. 2, May 1, 2009, pp. 175-179, XP026064568.

* cited by examiner

FIG. 3

(A)
```
                    141                   165
                    8330                  8354
EF600696    ACACCCTGAGCTGCTCACCTCACCT (SEQ ID NO:64)
DQ287255    CAC..TGAGCTGCTGC......... (SEQ ID NO:65)
DQ287261    ...T..................... (SEQ ID NO:66)
D00647      .........................
DQ287257    CACT..................... (SEQ ID NO:67)
AF257515    .........................
DQ287260    .........................
DQ288220    .T..............TT....... (SEQ ID NO:68)
M38278      ..G...................... (SEQ ID NO:69)
DQ287259    CAC..TGT................. (SEQ ID NO:70)
DQ288193    .......A................. (SEQ ID NO:71)
```

Consensus    MNMYCYKDRSYKSYKSAYYTCACCT
             (SEQ ID NO:1)

CoCoMo6      5'-MNMYCYKDRSYKSYKSAYYTCACCT-3'

(B)
```
                    240           254
                    8429          8443
EF600696    CTCAGCTCTCGGTCC (SEQ ID NO:4)
DQ287255    ...............
DQ287261    ...............
D00647      ...............
DQ287257    ...............
AF257515    ...............
DQ287260    ...............
DQ288220    ...............
M38278      ...............
DQ287259    ...............
DQ288193    ...............
```

Consensus    CTCAGCTCTCGGTCC
             (SEQ ID NO:4)

FAM-BLV-MGB  5'-CTCAGCTCTCGGTCC-3'

(C)
```
                    284                   308
                    8473                  8497
EF600696    TCGGCTATCCGGCAGCGGTCAGGTA (SEQ ID NO:72)
DQ287255    .........................
DQ287261    .........................
D00647      ..............GC.G....... (SEQ ID NO:73)
DQ287257    .........................
AF257515    ..............C.......... (SEQ ID NO:74)
DQ287260    ..............A.......... (SEQ ID NO:75)
DQ288220    .........................
M38278      .........................
DQ287259    .........................
DQ288193    .........................
```

Consensus    TCGGCTATCCGSMAGSSGKCAGGTA (SEQ ID NO:76)

CoCoMo81     3'-AGCCGATAGGCSKTCSSCMGTCCAT-5'

FIG. 8

SEQUENCE LISTING

```
<160> NUMBER OF SEQ ID NOS: 84

<210> SEQ ID NO 1
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is a, c, g, or t

<400> SEQUENCE: 1
mnmycykdrs yksyksayyt cacct                                        25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
tacctgmcss ctkscggata gccga                                        25

<210> SEQ ID NO 3
<211> LENGTH: 14
<212> TYPE: DNA
<213> ORGANISM: Artificial Sequence
<220> FEATURE:
<223> OTHER INFORMATION: probe

<400> SEQUENCE: 3
ctcagctctc ggtc                                                    14

<210> SEQ ID NO 4
<211> LENGTH: 15
```

```
<212> TYPE: DNA
<213> ORGANISM: Artificial Sequence
<220> FEATURE:
<223> OTHER INFORMATION: probe

<400> SEQUENCE: 4
ctcagctctc ggtcc                                                     15

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cccagagacc acagagaatg c                                              21

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
cccaccagag ccacaatca                                                 19

<210> SEQ ID NO 7
<211> LENGTH: 14
<212> TYPE: DNA
<213> ORGANISM: Artificial Sequence
<220> FEATURE:
<223> OTHER INFORMATION: primer

<400> SEQUENCE: 7
tgtgtgccct gggc                                                      14

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
cccgctcgag tgtatgaaag atcatgccga                                     30

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
cgggatcctg tttgccggtc tctcctgg                                       28

<210> SEQ ID NO 10
<211> LENGTH: 21
<212> TYPE: DNA
<213> ORGANISM: Artificial Sequence
<220> FEATURE:
<223> OTHER INFORMATION: primer
```

<400> SEQUENCE: 10
tgtatgaaag atcatgycgr c                                          21

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
aattgtttgc cggtctctc                                             19

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gagctctctt gctcccgaga c                                          21

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gaaacaaacg cgggtgcaag ccag                                       24

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
aacgtcagct gccagaaa                                              18

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aaaatccaca ccctgagctg                                            20

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
accgagcccc caattgttt                                             19

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
acctgyygwk aaaytaatam aatgc    25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
cydkysrgyt arcggcrcca gaagc    25

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
gsccydkysr gytarcggcr ccaga    25

<210> SEQ ID NO 20
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(11)
<223> OTHER INFORMATION: n is a, c, g, or t

<400> SEQUENCE: 20
vrraawhymm nmycykdagc tgctg    25

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
kddwaahtwa wwmaawkscg gccct    25

<210> SEQ ID NO 22
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (14)..(14)
<223> OTHER INFORMATION: n is a, c, g, or t

<400> SEQUENCE: 22
yysvrraawh ymmnmycykd agctg                               25

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
gctcccgagr ccttctggtc ggcta                               25

<210> SEQ ID NO 24
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t

<400> SEQUENCE: 24
nmycykdrsy ksyksayytc acctg                               25

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
sgkycygagy yykcttgctc ccgag                               25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
ysgkycygag yyykcttgct cccga                               25

<210> SEQ ID NO 27
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 27
hvvrrwmhhy mmnmyshknw gctgc                               25

<210> SEQ ID NO 28

```
<211> LENGTH: 25
<212> TYPE: DNA
<213> ORGANISM: Artificial Sequence
<220> FEATURE:
<223> OTHER INFORMATION: primer

<400> SEQUENCE: 28
yyysgkycyg agyyykcttg ctccc                                            25

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
sgsmvcmrra rsbrytctyy tcctg                                            25

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
yyyysgkycy gagyyykctt gctcc                                            25

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
vcmrrarsbr ytctyytcct gagac                                            25

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
gsmvcmrrar sbrytctyyt cctga                                            25

<210> SEQ ID NO 33
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 33
mnmymydnvs ykvbbbryyk cacct                                            25
```

```
<210> SEQ ID NO 34
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t

<400> SEQUENCE: 34
ysbrrgbybk ytykcdscng agacc                                              25

<210> SEQ ID NO 35
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: n is a, c, g, or t

<400> SEQUENCE: 35
bysbrrgbyb kytykcdscn gagac                                              25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
yyyybgbyyy swghyybcky gctcc                                              25

<210> SEQ ID NO 37
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 37
vrdnyhhnhy yybnrkyyby tgacc                                              25

<210> SEQ ID NO 38
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
```

```
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 38
hvvnvhvnhh vvnvnsnknw gmygs                                  25

<210> SEQ ID NO 39
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 39
nnhhdhbhrw dmmahnsmbd smsyk                                  25

<210> SEQ ID NO 40
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 40
bnnvbbhvnv hnyyybnyhv mybhs                                  25

<210> SEQ ID NO 41
<211> LENGTH: 25
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 41
nvmnbnnhhv dnhwmhysmb rmsct                                    25

<210> SEQ ID NO 42
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 42
nnnbbhvbvn nhnbbrhyyb tctcc                                    25

<210> SEQ ID NO 43
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t

<400> SEQUENCE: 43
tggtctchgc ygagarccnc cctcc                                    25

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
gccgaccaga aggyctcggg agcaa                                    25

<210> SEQ ID NO 45
<211> LENGTH: 25
<212> TYPE: DNA
<213> ORGANISM: Artificial Sequence
<220> FEATURE:
```

```
<223> OTHER INFORMATION: primer

<400> SEQUENCE: 45
sssrkkbvvr vscmrrmssc cttgg                                25

<210> SEQ ID NO 46
<211> LENGTH: 25
<212> TYPE: DNA
<213> ORGANISM: Artificial Sequence
<220> FEATURE:
<223> OTHER INFORMATION: primer

<400> SEQUENCE: 46
kkbvvrvscm rrmssccttg gagcg                                25

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
gmcssctksc ggatagccga ccaga                                25

<210> SEQ ID NO 48
<211> LENGTH: 25
<212> TYPE: DNA
<213> ORGANISM: Artificial Sequence
<220> FEATURE:
<223> OTHER INFORMATION: primer

<400> SEQUENCE: 48
cctgmcssct kscggatagc cgacc                                25

<210> SEQ ID NO 49
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n is a, c, g, or t

<400> SEQUENCE: 49
yyymmvmvbb kknbtdkcct tacct                                25

<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50
rmvvrdvbvv gvbdsmvrsc cwkrs                                25

<210> SEQ ID NO 51
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
```

<222> LOCATION: (9)..(9)
<223> OTHER INFORMATION: n is a, c, g, or t

<400> SEQUENCE: 51
vmvvvdrvnv ssvdkvmrvs cywgr                    25

<210> SEQ ID NO 52
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t

<400> SEQUENCE: 52
yymmvmvbbk knbtdkcctt acctg                    25

<210> SEQ ID NO 53
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 53
vvvrrnbsvr rbbvvrvscc mkwsg                    25

<210> SEQ ID NO 54
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t

<400> SEQUENCE: 54
nknvvrvscv vvvvvvswkr gagcg                    25

<210> SEQ ID NO 55
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:

```
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (16)..(20)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 55
nnvvndrvnv bnndknnnnn bhnnd                                25

<210> SEQ ID NO 56
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(7)
<223> OTHER INFORMATION: n is a, c, g, or t

<400> SEQUENCE: 56
bhyyybnsss vhkvsrgrkm gccga                                25

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
drrrsyhvsv rdrstcdsdr ccgag                                25

<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58
wwvvdshyss vkksskswyw gccga                                25

<210> SEQ ID NO 59
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(5)
<223> OTHER INFORMATION: n is a, c, g, or t

<400> SEQUENCE: 59
nhnnnbbbss vvtrgwsksh gccga                                25

<210> SEQ ID NO 60
<211> LENGTH: 25
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 60
nrrrvbhvvv rdrsyynsdr ccgag                                  25

<210> SEQ ID NO 61
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 61
nhnnnbbbss vnydswsbbn gccga                                  25

<210> SEQ ID NO 62
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 62
vmvvvndnnv ssvddvmvvv cywgr                                  25

<210> SEQ ID NO 63
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(7)
<223> OTHER INFORMATION: n is a, c, g, or t

<400> SEQUENCE: 63
```
vvvrrnnvvr dbbvvvvbss mkwsg          25

<210> SEQ ID NO 64
<211> LENGTH: 25
<212> TYPE: DNA
<213> ORGANISM: Bovine Leukemia Virus

<400> SEQUENCE: 64
acaccctgag ctgctgacct cacct          25

<210> SEQ ID NO 65
<211> LENGTH: 25
<212> TYPE: DNA
<213> ORGANISM: Bovine Leukemia Virus

<400> SEQUENCE: 65
caccctgagc tgctgcacct cacct          25

<210> SEQ ID NO 66
<211> LENGTH: 25
<212> TYPE: DNA
<213> ORGANISM: Bovine Leukemia Virus

<400> SEQUENCE: 66
acatcctgag ctgctgacct cacct          25

<210> SEQ ID NO 67
<211> LENGTH: 25
<212> TYPE: DNA
<213> ORGANISM: Bovine Leukemia Virus

<400> SEQUENCE: 67
cactcctgag ctgctgacct cacct          25

<210> SEQ ID NO 68
<211> LENGTH: 25
<212> TYPE: DNA
<213> ORGANISM: Bovine Leukemia Virus

<400> SEQUENCE: 68
ataccctgag ctgctgattt cacct          25

<210> SEQ ID NO 69
<211> LENGTH: 25
<212> TYPE: DNA
<213> ORGANISM: Bovine Leukemia Virus

<400> SEQUENCE: 69
agaccctgag ctgctgacct cacct          25

<210> SEQ ID NO 70
<211> LENGTH: 25
<212> TYPE: DNA
<213> ORGANISM: Bovine Leukemia Virus

<400> SEQUENCE: 70
caccctgtag ctgctgacct cacct          25

<210> SEQ ID NO 71
<211> LENGTH: 25
<212> TYPE: DNA
<213> ORGANISM: Bovine Leukemia Virus

<400> SEQUENCE: 71

```
acaccctaag ctgctgacct cacct                                          25

<210> SEQ ID NO 72
<211> LENGTH: 25
<212> TYPE: DNA
<213> ORGANISM: Bovine Leukemia Virus

<400> SEQUENCE: 72
tcggctatcc ggcagcggtc aggta                                          25

<210> SEQ ID NO 73
<211> LENGTH: 25
<212> TYPE: DNA
<213> ORGANISM: Bovine Leukemia Virus

<400> SEQUENCE: 73
tcggctatcc ggcaggcggc aggta                                          25

<210> SEQ ID NO 74
<211> LENGTH: 25
<212> TYPE: DNA
<213> ORGANISM: Bovine Leukemia Virus

<400> SEQUENCE: 74
tcggctatcc gccagcggtc aggta                                          25

<210> SEQ ID NO 75
<211> LENGTH: 25
<212> TYPE: DNA
<213> ORGANISM: Bovine Leukemia Virus

<400> SEQUENCE: 75
tcggctatcc ggaagcggtc aggta                                          25

<210> SEQ ID NO 76
<211> LENGTH: 25
<212> TYPE: DNA
<213> ORGANISM: Bovine Leukemia Virus

<400> SEQUENCE: 76
tcggctatcc gsmagssgkc aggta                                          25

<210> SEQ ID NO 77
<211> LENGTH: 531
<212> TYPE: DNA
<213> ORGANISM: Bovine Leukemia Virus

<400> SEQUENCE: 77
tgtatgaaag atcatgccga cctaggcgcc gccaccgccc cgtaaaccag acagagacgt    60
cagctgccag aaaagctggt gacggcagct ggtggctaga atccccgtac ctccccaact   120 tccccttttcc cgaaaaatcc acaccctgag ctgctgacct cacctgctga taaattaata  180
aaatgccggc cctgtcgagt tagcggcacc agaagcgttc ttctcctgag accctcgtgc   240
tcagctctcg gtcctgagct ctcttgctcc cgagaccttc tggtcggcta tccggcagcg   300
gtcaggtaag gcaaaccacg gtttggaggg tggttctcgg ctgagaccac cgcgagctct   360
atctccggtc ctctgaccgt ctccacgtgg actctctcct ttgcctcctg accccgcgct   420
ccaagggcgt ctggcttgca cccgcgtttg tttcctgtct tactttctgt ttctcgcggc   480
ccgcgctctc tccttcggcg ccctctagcg gccaggagag accggcaaac a            531
```

<210> SEQ ID NO 78
<211> LENGTH: 451
<212> TYPE: DNA
<213> ORGANISM: Bovine Leukemia Virus

<400> SEQUENCE: 78

```
agctggtgac ggcagctggt ggctagaatc cccgcacctc cccaacttcc cctttcccga      60
gaaatccaca ccctgagctg ctgacctcac ctgctgataa actaataaaa tgccggccct     120
gtcgagttag cggcaccaga agcgttcttc tcctgagacc ctcgtgctca gctctcggtc     180
ctgagctctc ttgctcccga gaccttctgg tcggctatcc ggcagcggtc aggtaaggca     240
aaccacggtt ggagggtggt tctcggctga gaccactgcg agctctatct ccggtccttg     300
accgtctcca cgtggactct ctctcttgcc tcctgacccc gcgctccaag ggcgtctggc     360
ttgcacccgc gttcgtttcc tgtcttactt tctgtttctc gcggcccgcg ctctctcctc     420
cggcgccctc tagcggccag gagagaccgg c                                    451
```

<210> SEQ ID NO 79
<211> LENGTH: 451
<212> TYPE: DNA
<213> ORGANISM: Bovine Leukemia Virus

<400> SEQUENCE: 79

```
agctggtgac ggcagctggt ggctagaatc cccgaacctc cccaacttcc cctttcccga      60
gaaatccaca ccctgagctg ctgacctcac ctgctgataa attaataaaa tgccggccct     120
gtcgagttag cggcaccaga agcgttcttc tcctgagacc ctcgtgctca gctctcggtc     180
ctgagctctc ttgctcccga gaccttctgg tcggctatcc ggcagcggtc aggtaaggca     240
aaccacggtt ggagggtggt tctcggctga gaccactgcg agctctatct ccggtccttg     300
accgtctcca cgtggactct ttctcttgcc tcctgacccc gcgctccaag ggcgtctggc     360
ttgcacccgc gttcgtttcc tgtcttactt tctgtttctc gcggcccgcg ctctctcctc     420
cggcgccctc tagcggccag gagagaccgg c                                    451
```

<210> SEQ ID NO 80
<211> LENGTH: 453
<212> TYPE: DNA
<213> ORGANISM: Bovine Leukemia Virus

<400> SEQUENCE: 80

```
agctggtgac ggcagctggt ggctagaatc cccgtacctc cccaacttcc cctttcccga      60
aaaatccaca ccctgagctg ctgacctcac ctgctgataa attaataaaa tgccggccct     120
gtcgagttag cggcaccaga agcgttcttc tcctgagacc ctcgtgctca gctctcggtc     180
ctgagctctc ttgctcccga gaccttctgg tcggttatcc ggcagcggtc aggtaaggca     240
aaccacggtt tggagggtgg ttctcggctg agaccaccgc gagctctatc tccggtcctc     300
cgaccgtctc cacgtggact ctctctcttg cctcctgacc ccgcgctcca agggcgtctg     360
gcttgcaccc gcgtttgttt cctgtcttac tttctgtttc tcgcggcccg cgcgctctcc     420
ttcggcgccc tccagcggcc aggagagacc ggc                                  453
```

<210> SEQ ID NO 81
<211> LENGTH: 210
<212> TYPE: DNA
<213> ORGANISM: Bovine Leukemia Virus

<400> SEQUENCE: 81

```
agctggtgac ggcagctggt ggctagaatc cccgtacctc cccaacttcc cctttcccga      60
aaaatccaca ccctgagctg ctgacctcac ctgctgataa attaataaaa tgccggccct     120
gtcgagttag cggcaccaga agcgttcttc tcctgagacc ctcgtgctca gctctcggtc     180
ctgagctctc ttgctcccga gaccttctgg                                       210

<210> SEQ ID NO 82
<211> LENGTH: 373
<212> TYPE: DNA
<213> ORGANISM: Bovine Leukemia Virus

<400> SEQUENCE: 82
ctgacctcac ctgctgacaa attaataaaa tgccggccct gtcgagttag cggcaccaga      60
agcgttcttc tcctgagacc ctcgtgctca gctctcggtc ctgagctctc ttgctcccga     120
gaccttctgg tcggctatcc ggcagcggtc aggtaaggca agccacggtt tggagggtgg     180
ttctcggctg agaccaccgc gagctctatc tccggtcctc tgaccgtctc cacgtggact     240
ctctcctttg cctcctgacc ccgcgctccc agggcgtctg gcttgcaccc gcgtttgttt     300
cctgtctcac tttctgtttc tcgcggcccg cgctctctcc ctcggcgccc tctagcggcc     360
aggagagacc ggc                                                         373

<210> SEQ ID NO 83
<211> LENGTH: 118
<212> TYPE: DNA
<213> ORGANISM: Bovine Leukemia Virus

<400> SEQUENCE: 83
gctgataaat taataaaatg ccggccctgt cgagttagcg gcaccagaag cgttcttctc      60
ctgagaccct cgtgctcagc tctcggtcct gagctctctt gctcccgaga ccttctgg       118

<210> SEQ ID NO 84
<211> LENGTH: 117
<212> TYPE: DNA
<213> ORGANISM: Bovine Leukemia Virus

<400> SEQUENCE: 84
gctgacaaat taataaaatg ccggccctgt cgagttagcg gcaccagaag cgttcttctc      60
tgagaccctc gtgctcagct ctcggtcctg agctctcttg ctcccgagac cttctgg        117
```

KIT FOR DETECTING BOVINE LEUKEMIA VIRUS(BLV), AND USE THEREOF

CROSS-REFERENCE TO RELATED APPLICATIONS

This application is a national stage of International (PCT) Patent Application Serial No. PCT/JP2011/074887, filed Oct. 21, 2011, which claims the benefit of and priority to U.S. Provisional Patent Application No. 61/405,433 filed Oct. 21, 2010, the contents of each of which are hereby incorporated by reference for all purposes.

TECHNICAL FIELD

The present invention relates to kit for detecting bovine leukemia virus (BLV), and use thereof.

BACKGROUND ART

Bovine leukemia virus (BLV) is closely related to human T-cell leukemia virus types 1 and 2 (HTLV-1 and -2) and is the etiological agent of enzootic bovine leukosis (EBL), which is the most common neoplastic disease of cattle [Non-Patent Literature 9]. Infection with BLV can remain clinically silent, with cattle in an aleukemic state. It can also emerge as a persistent lymphocytosis (PL), characterized by an increased number of B lymphocytes, or more rarely, as a B-cell lymphoma in various lymph nodes after a long latent period [Non-Patent Literature 9].

In addition to the structural and enzymatic Gag, Pol, and Env proteins, BLV encodes at least two regulatory proteins, namely Tax and Rex, in the pX region located between the env gene and the 3' long terminal repeat (LTR) [Non-Patent Literature 9]. Moreover, BLV contains several other small open reading frames in the region between the env gene and the tax/rex genes in the pX region. These encode products designated as R3 and G4 [Non-Patent Literature 10]. BLV has two identical LTRs, which possess a U3 region, an unusually long R region, and a U5 region; these LTRs only exert efficient transcriptional promoter activity in cells productively infected with BLV [Non-Patent Literature 9]. BLV can integrate into dispersed sites within the host genome [Non-Patent Literature 11] and appears to be transcriptionally silent in vivo [Non-Patent Literature 12]. Indeed, transcription of the BLV genome in fresh tumor cells or in fresh peripheral blood mononuclear cells (PBMCs) from infected individuals is almost undetectable by conventional techniques [Non-Patent Literatures 12, 13]. In situ hybridization has revealed the expression of viral RNA at low levels in many cells and at a high level in a few cells in populations of freshly isolated PBMCs from clinically normal BLV-infected animals [Non-Patent Literature 14]. It appears that BLV provirus remains integrated in cellular genomes, even in the absence of detectable BLV antibodies. Therefore, in addition to the routine diagnosis of BLV infection using conventional serological techniques such as the immunodiffusion test [Non-Patent Literatures 15-18] and enzyme-linked immunosorbent assay (ELISA) [Non-Patent Literatures 17-20], diagnostic BLV PCR techniques that aim to detect the integrated BLV proviral genome within the host genome are also commonly used [Non-Patent Literatures 17-19, 21-23].

CITATION LIST

Non-Patent Literature

1. Lloyd-Smith J O, George D, Pepin K M, Pitzer V E, Pulliam J R, Dobson A P, Hudson P J, Grenfell B T: Epidemic dynamics at the human-animal interface. *Science* 2009, 326:1362-1367.
2. Tapper M L: Emerging viral diseases and infectious disease risks. *Haemophilia* 2006, 12 Suppl 1:3-7; discussion 26-28.
3. Endoh D, Mizutani T, Kirisawa R, Maki Y, Saito H, Kon Y, Morikawa S, Hayashi M: Species-independent detection of RNA virus by representational difference analysis using non-ribosomal hexanucleotides for reverse transcription. *Nucleic Acids Res* 2005, 33:e65.
4. Rose T M, Schultz E R, Henikoff J G, Pietrokovski S, McCallum C M, Henikoff S: Consensus-degenerate hybrid oligonucleotide primers for amplification of distantly related sequences. *Nucleic Acids Res* 1998, 26:1628-1635.
5. Bartl S: Amplification using degenerate primers with multiple inosines to isolate genes with minimal sequence similarity. *Methods Mol Biol* 1997, 67:451-457.
6. Moonka D, Loh E Y: A consensus primer to amplify both alpha and beta chains of the human T cell receptor. *J Immunol Methods* 1994, 169:41-51.
7. Rose T M, Henikoff J G, Henikoff S: CODEHOP (COnsensus-DEgenerate Hybrid Oligonucleotide Primer) PCR primer design. *Nucleic Acids Res* 2003, 31:3763-3766.
8. Katoh K, Toh H: Recent developments in the MAFFT multiple sequence alignment program. *Brief Bioinform* 2008, 9:286-298.
9. Gillet N, Florins A, Boxus M, Burteau C, Nigro A, Vandermeers F, Balon H, Bouzar A B, Defoiche J, Burny A, et al: Mechanisms of leukemogenesis induced by bovine leukemia virus: prospects for novel anti-retroviral therapies in human. *Retrovirology* 2007, 4:18.
10. Alexandersen S, Carpenter S, Christensen J, Storgaard T, Viuff B, Wannemuehler Y, Belousov J, Roth J A: Identification of alternatively spliced mRNAs encoding potential new regulatory proteins in cattle infected with bovine leukemia virus. *J Virol* 1993, 67:39-52.
11. Kettmann R, Meunier-Rotival. M, Cortadas J, Cuny G, Ghysdael J, Mamerickx M, Burny. A, Bernardi G: Integration of bovine leukemia virus DNA in the bovine genome. *Proc Natl Acad Sci USA* 1979, 76:4822-4826.
12. Kettmann R, Deschamps J, Cleuter Y, Couez D, Burny A, Marbaix G: Leukemogenesis by bovine leukemia virus: proviral DNA integration and lack of RNA expression of viral long terminal repeat and 3' proximate cellular sequences. *Proc Natl Acad Sci USA* 1982, 79:2465-2469.
13. Kettmann R, Cleuter Y, Mamerickx M, Meunier-Rotival M, Bernardi G, Burny A, Chantrenne H: Genomic integration of bovine leukemia provirus: comparison of persistent lymphocytosis with lymph node tumor form of enzootic. *Proc Natl Acad Sci USA* 1980, 77:2577-2581.
14. Lagarias D M, Radke K: Transcriptional activation of bovine leukemia virus in blood cells from experimentally infected, asymptomatic sheep with latent infections. *J Virol* 1989, 63:2099-2107.
15. Aida Y, Miyasaka M, Okada K, Onuma M, Kogure S, Suzuki M, Minoprio P, Levy D, Ikawa Y: Further phenotypic characterization of target cells for bovine leukemia virus experimental infection in sheep. *Am J Vet Res* 1989, 50:1946-1951.
16. Wang C T: Bovine leukemia virus infection in Taiwan: epidemiological study. *J Vet Med Sci* 1991, 53:395-398.
17. Monti G E, Frankena K, Engel B, Buist W, Tarabla H D, de Jong M C: Evaluation of a new antibody-based enzyme-linked immunosorbent assay for the detection of bovine leukemia virus infection in dairy cattle. *J Vet Diagn Invest* 2005, 17:451-457.
18. Kurdi A, Blankenstein P, Marquardt O, Ebner D: [Serologic and virologic investigations on the presence of BLV infection in a dairy herd in Syria]. *Berl Munch Tierarztl Wochenschr* 1999, 112:18-23.
19. Zaghawa A, Beier D, Abd El-Rahim I H, Karim I, El-ballal S, Conraths F J, Marquardt O: An outbreak of enzootic bovine leukosis in upper Egypt: clinical, laboratory and molecular-epidemiological studies. *J Vet Med B Infect Dis Vet Public Health* 2002, 49:123-129.
20. Schoepf K C, Kapaga A M, Msami H M, Hyera J M: Serological evidence of the occurrence of enzootic bovine leukosis (EBL) virus infection in cattle in Tanzania. *Trop Anim Health Prod* 1997, 29:15-19.
21. Tajima S, Aida Y: The region between amino acids 245 and 265 of the bovine leukemia virus (BLV) tax protein restricts transactivation not only via the BLV enhancer but also via other retrovirus enhancers. *J Virol* 2000, 74:10939-10949.
22. Tajima S, Takahashi M, Takeshima S N, Konnai S, Yin S A, Watarai S, Tanaka Y, Onuma M, Okada K, Aida Y: A mutant form of the tax protein of bovine leukemia virus (BLV), with enhanced transactivation activity, increases expression and propagation of BLV in vitro but not in vivo. *J Virol* 2003, 77:1894-1903.
23. Tajima S, Ikawa Y, Aida Y: Complete bovine leukemia virus (BLV) provirus is conserved in BLV-infected cattle throughout the course of B-cell lympho sarcoma development. *J Virol* 1998, 72:7569-7576.
24. Moratorio G, Obal G, Dubra A, Correa A, Bianchi S, Buschiazzo A, Cristina J, Pritsch O: Phylogenetic analysis of bovine leukemia viruses isolated in South America reveals diversification in seven distinct genotypes. *Arch Virol* 2010, 155:481-489.
25. VanLeeuwen J A, Tiwari A, Plaizier J C, Whiting T L: Seroprevalences of antibodies against bovine leukemia virus, bovine viral diarrhea virus, *Mycobacterium avium* subspecies paratuberculosis, and *Neospora caninum* in beef and dairy cattle in Manitoba. *Can Vet J* 2006, 47:783-786.
26. Kobayashi S, Tsutsui T, Yamamoto T, Hayama Y, Kameyama K, Konishi M, Murakami K: Risk factors associated with within-herd transmission of bovine leukemia virus on dairy farms in Japan. *BMC Vet Res* 2010, 6:1.
27. Rodriguez S M, Golemba M D, Campos R H, Trono K, Jones L R: Bovine leukemia virus can be classified into seven genotypes: evidence for the existence of two novel clades. *J Gen Virol* 2009, 90:2788-2797.
28. Coulston J, Naif H, Brandon R, Kumar S, Khan S, Daniel R C, Lavin M F: Molecular cloning and sequencing of an Australian isolate of proviral bovine leukaemia virus DNA: comparison with other isolates. *J Gen Virol* 1990, 71 (Pt 8):1737-1746.
29. Asfaw Y, Tsuduku S, Konishi M, Murakami K, Tsuboi T, Wu D, Sentsui H: Distribution and superinfection of bovine leukemia virus genotypes in Japan. *Arch Virol* 2005, 150:493-505.
30. Tong S, Chern S W, Li Y, Pallansch M A, Anderson L J: Sensitive and broadly reactive reverse transcription-PCR assays to detect novel paramyxoviruses. *J Clin Microbiol* 2008, 46:2652-2658.
31. Lew A, Bock R, Miles J, Cuttell L, Steer P, Nadin-Davis S: Sensitive and specific detection of bovine immunodeficiency virus and bovine syncytial virus by 5' Taq nuclease assays with fluorescent 3' minor groove binder-DNA probes. *J Virol Methods* 2004, 116:1-9
32. Moens B, Lopez G, Adaui V, Gonzalez E, Kerremans L, Clark D, Verdonck K, Gotuzzo E, Vanham G, Cassar O, et al: Development and validation of a multiplex real-time PCR assay for simultaneous genotyping and human T-lymphotropic virus type 1, 2, and 3 proviral load determination. *J Clin Microbiol* 2009, 47:3682-3691.
33. Dehee A, Cesaire R, Desire N, Lezin A, Bourdonne O, Sera O, Plumelle Y, Smadja D, Nicolas J C: Quantitation of HTLV-I proviral load by a TaqMan real-time PCR assay. *J Virol Methods* 2002, 102:37-51.
34. Inabe K, Ikuta K, Aida Y: Transmission and propagation in cell culture of virus produced by cells transfected with an infectious molecular clone of bovine leukemia virus. *Virology* 1998, 245:53-64.
35. Aida Y, Okada K, Onuma M: Antigenic regions defined by monoclonal antibodies on tumor-associated antigens of bovine leukemia virus-induced lymphosarcoma cells. *Leuk Res* 1993, 17:187-193.
36. Aida Y, Okada K, Ohtsuka M, Amanuma H: Tumor-associated M(r) 34,000 and M(r) 32,000 membrane glycoproteins that are serine phosphorylated specifically in bovine leukemia virus-induced lymphosarcoma cells. *Cancer Res* 1992, 52:6463-6470.
37. Aida Y, Okada K, Amanuma H: Phenotype and ontogeny of cells carrying a tumor-associated antigen that is expressed on bovine leukemia virus-induced lymphosarcoma. *Cancer Res* 1993, 53:429-437.
38. Aida Y, Onuma M, Mikami T, Izawa H: Topographical analysis of tumor-associated antigens on bovine leukemia virus-induced bovine lymphosarcoma. *Cancer Res* 1985, 45:1181-1186.
39. Aida Y, Nishino Y, Amanuma H, Murakami K, Okada K, Ikawa Y: The role of tumor-associated antigen in bovine leukemia virus-induced lymphosarcoma. *Leukemia* 1997, 11 Suppl 3:216-218.
40. Tajima S, Zhuang W Z, Kato M V, Okada K, Ikawa Y, Aida Y: Function and conformation of wild-type p53 protein are influenced by mutations in bovine leukemia virus-induced B-cell lymphosarcoma. *Virology* 1998, 243: 735-746.
41. Konnai S, Usui T, Ikeda M, Kohara J, Hirata T, Okada K, Ohashi K, Onuma M: Tumor necrosis factor-alpha genetic polymorphism may contribute to progression of bovine leukemia virus-infection. *Microbes Infect* 2006, 8:2163-2171.
42. Levy D, Deshayes L, Guillemain B, Parodi A L: Bovine leukemia virus specific antibodies among French cattle. I. Comparison of complement fixation and hematological tests. *Int J Cancer* 1977, 19:822-827.
43. Miyasaka M, Reynolds. J, Dudler L, Beya M F, Leiserson W, Trnka Z: Differentiation of B lymphocytes in sheep. II. Surface phenotype of B cells leaving the 'bursa-equivalent' lymphoid tissue of sheep, ileal Peyer's patches. *Adv Exp Med Biol* 1985, 186:119-126.
44. Onuma. M, Koyama H, Aida Y, Okada K, Ogawa Y, Kirisawa R, Kawakami Y: Establishment of B-cell lines from tumor of enzootic bovine leukosis. *Leuk Res* 1986, 10:689-695.
45. Hughes S H, Shank P R, Spector D H, Kung H J, Bishop J M, Varmus H E, Vogt P K, Breitman M L: Proviruses of avian sarcoma virus are terminally redundant, co-extensive with unintegrated linear DNA and integrated at many sites. *Cell* 1978, 15:1397-1410.
46. Derse D, Diniak A J, Casey J W, Deininger P L: Nucleotide sequence and structure of integrated bovine leukemia virus long terminal repeats. *Virology* 1985, 141:162-166.
47. Aida Y, Kohda C, Morooka A, Nakai Y, Ogimoto K, Urao T, Asahina M: Cloning of cDNAs and the molecular evolution of a bovine MHC class II DRA gene. *Biochem Biophys Res Commun* 1994, 204:195-202.
48. Zhao T M, Robinson M A, Bowers F S, Kindt T J: Characterization of an infectious molecular clone of human T-cell leukemia virus type I. *J Virol* 1995, 69:2024-2030.
49. Adachi A, Gendelman H E, Koenig S, Folks T, Willey R, Rabson A, Martin M A: Production of acquired immunodeficiency syndrome-associated retrovirus in human and nonhuman cells transfected with an infectious molecular clone. *J Virol* 1986, 59:284-291.
50. Guan Y, Whitney J B, Detorio M, Wainberg M A: Construction and in vitro properties of a series of attenuated simian immunodeficiency viruses with all accessory genes deleted. *J Virol* 2001, 75:4056-4067.
51. Yanagawa S, Kakimi K, Tanaka H, Murakami A, Nakagawa Y, Kubo Y, Yamada Y, Hiai H, Kuribayashi K, Masuda T, et al.: Mouse mammary tumor virus with rearranged long terminal repeats causes murine lymphomas. *J Virol* 1993, 67:112-118.
52. Shackleford G M, Varmus H E: Construction of a clonable, infectious, and tumorigenic mouse mammary tumor virus provirus and a derivative genetic vector. *Proc Natl Acad Sci USA* 1988, 85:9655-9659.

SUMMARY OF INVENTION

Technical Problem

BLV infects cattle worldwide, imposing a severe economic impact on the dairy cattle industry [Non-Patent Literatures 16-20, 24-26]. Recent studies on the genetic variability of the BLV env gene have shown genetic variations among BLV isolates from different locations worldwide [Non-Patent Literatures 24, 27]. Further, as described above, the BLV enters a latent stage immediately after infection, and the BLV antigen and mRNA hardly are expressed in the cattle. Hence, accurate detection and quantification of BLV has been difficult to be performed depending on an amount of BLV antigen, an expression level of BLV mRNA, etc.

Therefore, to understand the mechanism of BLV-induced leukemogenesis and carry out the selection of BLV-infected animals, a detailed evaluation of changes in proviral load throughout the course of disease in BLV-infected cattle is required.

However, primers well addressing BLV diversity have not been developed, largely due to the high rate of mutation of BLV. And also, real-time quantitative PCR for BLV provirus has not been developed, largely due to differences in amplification efficiency caused by DNA sequence variations between clinical samples.

The present invention was made in order to solve the foregoing problems, and an object of the present invention is to provide new kit for detecting BLV, well addressing BLV diversity, and use thereof.

Further, another object of the present invention is to use the kit to develop a new quantitative real-time PCR method to measure the proviral load of almost all BLV variants.

Solution to Problem

In order to solve the foregoing problems, the present invention provides: a kit for detecting Bovine leukemia virus (BLV) including a first PCR primer including successive 20 bases or more in the base sequence denoted by SEQ ID NO: 1, the first PCR primer being oligonucleotide having 50 bases or less; and second PCR primer including successive 20 bases or more in the base sequence denoted by SEQ ID NO: 2, the second PCR primer being oligonucleotide having 50 bases or less. Further, the first PCR primer and the second PCR primer are both degenerate primers preferably.

Labeled arrows indicate the orientation and length of each primer. The black filled box indicates the probe annealing position. (A) The proviral structure of BLV in the BLV cell line FLK-BLV subclone pBLV913, complete genome [DDBJ: EF600696]. It contains two LTR regions at nucleotide positions 1-531 and 8190-8720. Lowercase labels indicate these LTR regions. The upper number shows the position of the 5' LTR and the lower number shows the position of the 3'LTR. Both LTRs include the U3, R and U5 regions. A triplicate 21-bp motif known as the Tax-responsive element (TRE) is present in the U3 region of the 5' LTR. The target region for amplification was in the U3 and R region, and the TaqMan™ probe for detecting the PCR product was from the R region. (B) The schematic outline of the bovine major histocompatibility complex (BoLA)-DRA gene (upper) and its cDNA clone MR1 [DDBJ: D37956] (lower). Exons are shown as open boxes. The numbers indicate the numbering of the nucleotide sequence of MR1. 5'UT, 5'-untranslated region; SP, signal sequence; α1, first domain; α2, second domain; CP, connecting peptide; TM, transmembrane domain; CY, cytoplasmic domain; 3'UT, 3-untranslated region. The target regions for amplification and for binding of the TaqMan™ probe to detect the PCR product are in exon 4.

Figure 2:
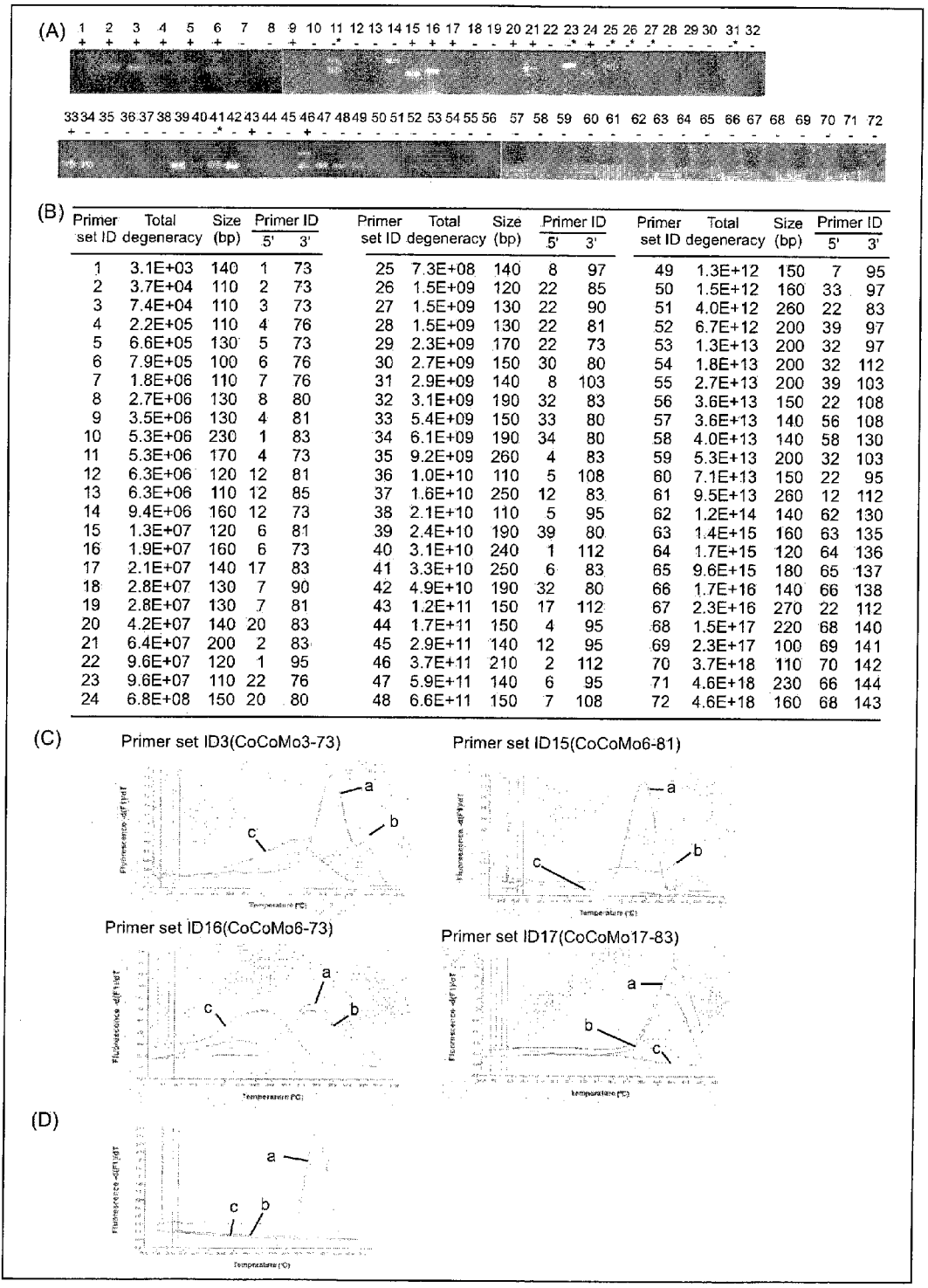

FIG. 2 relates to selection of the primer set for amplification of the BLV-LTR region.

(A) Touch-down PCR was performed using 72 primer sets with 49 primers designed by the CoCoMo program as shown in Table 1. PCR products were detected by electrophoresis on a 3% agarose gel. Lanes 1-72, 1-72 primer set ID; +, results positive for PCR product; −, negative results for same. *, designates PCR products that were detected but for which the amplicon sizes differed from the predicted size. (B) Summary of results shown in (A). Primer set IDs are arranged according to the degeneracy of the primer set and size of the PCR products. (C) The 4 representative melting curves with 16 primer sets of: BLV-infected BLSC-KU-17 cells (a), BLV-free normal cattle cells (b), and reagent-only as negative control (c). The specificity of the 16 selected primer sets was checked by melting curve analysis. Each PCR amplification was followed by gradual product melting at up to 95° C. (D) The optimization of PCR amplification with primer set ID 15 (CoCoMo 6 and 81). The melting curve of PCR products from BLV-infected BLSC-KU-17 cells (a), the BLV-free normal cattle Ns118 (b), and reagent-only as negative control (c).

FIG. 3 relates to sequence alignment of annealing positions of the CoCoMo 6 primer (A), FAM-BLV-MGB probe (B) and CoCoMo 81 primer (C) in the 52 BLV LTR sequences.

The sequence alignment used 52 sequences from GenBank that were integrated in a total of 11 sequences, including 8 individual sequences for the CoCoMo 6 primer and 4 individual sequences for the CoCoMo81 primer. Accession numbers for the representative sequences are indicated in the left column. Numbers indicate the numbering of the nucleotide sequence of the FLK-BLV subclone pBLV913 [DDBJ: EF600696]. The upper number shows the position of the 5' LTR and the lower number shows the position of the 3' LTR.

Figure 4:
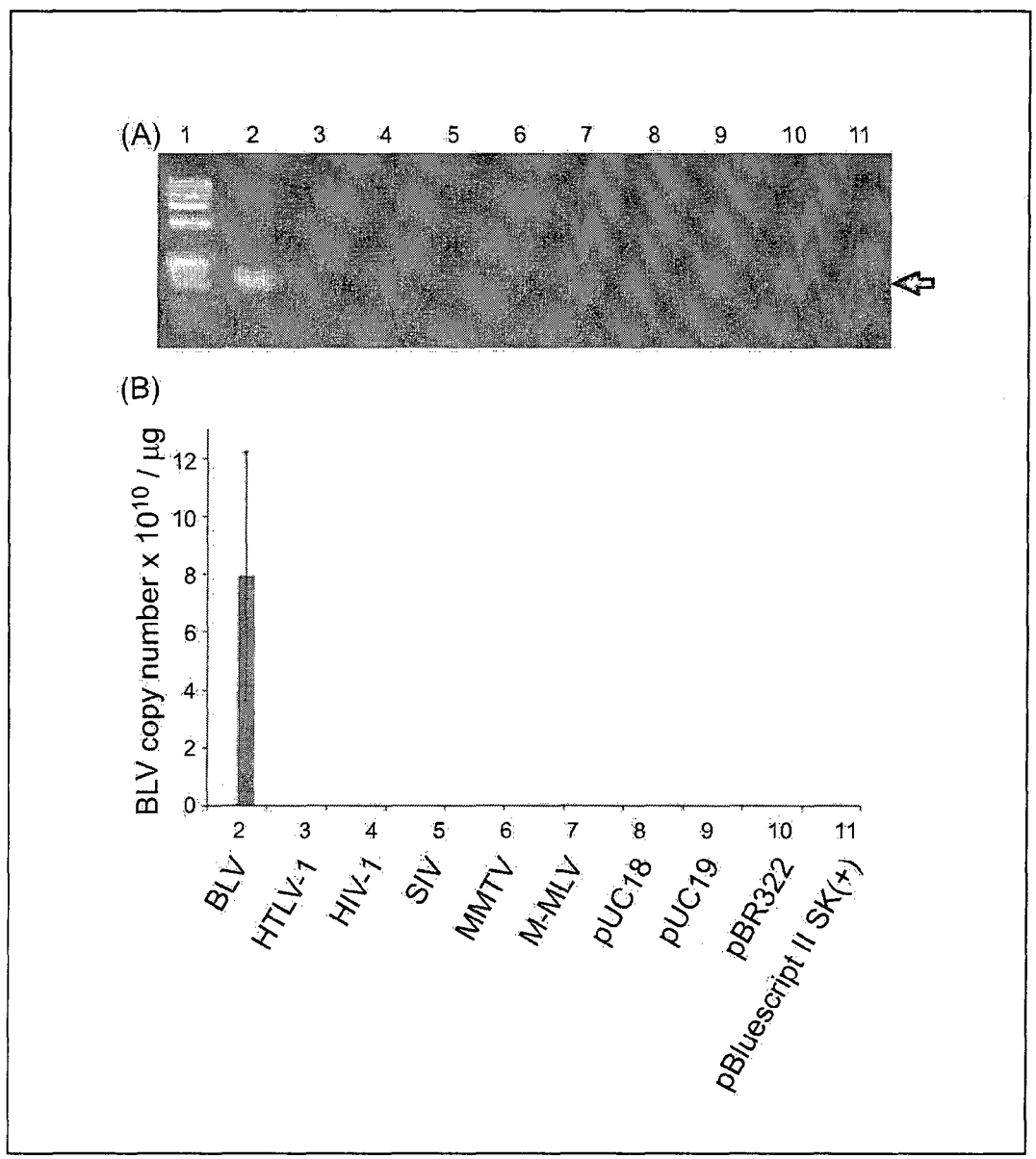

FIG. 4 relates to evaluation of the specificity of the BLV-CoCoMo-qPCR primers.

(A) Real-time PCR using the CoCoMo 6 and CoCoMo 81 primers from the BLV-CoCoMo-qPCR was performed using 0.3 ng of the following infectious molecular clones: BLV (pBLV-IF, lane 2); HTLV-1 (pK30, lane 3); HIV-1 (pNL4-3, lane 4); SIV (pSIVmac239/WT, lane 5); MMTV (hybrid MMTV, lane 6); M-MLV (pL-4, lane 7); and the plasmids pUC18 (lane 8), pUC19 (lane 9), pBR322 (lane 10), and pBluescript SK(+) (lane 11). PCR products were subjected to 3% agarose gel electrophoresis. Lane 1, DNA marker Φx174-Hae III digest. A PCR product 168 bp in length is indicated by an arrow. (B) The number of BLV provirus copies in 1 μg of DNA from each DNA sample is indicated by lowercase. Values represent the mean+standard deviation (SD) of the results of three independent experiments.

Figure 5:
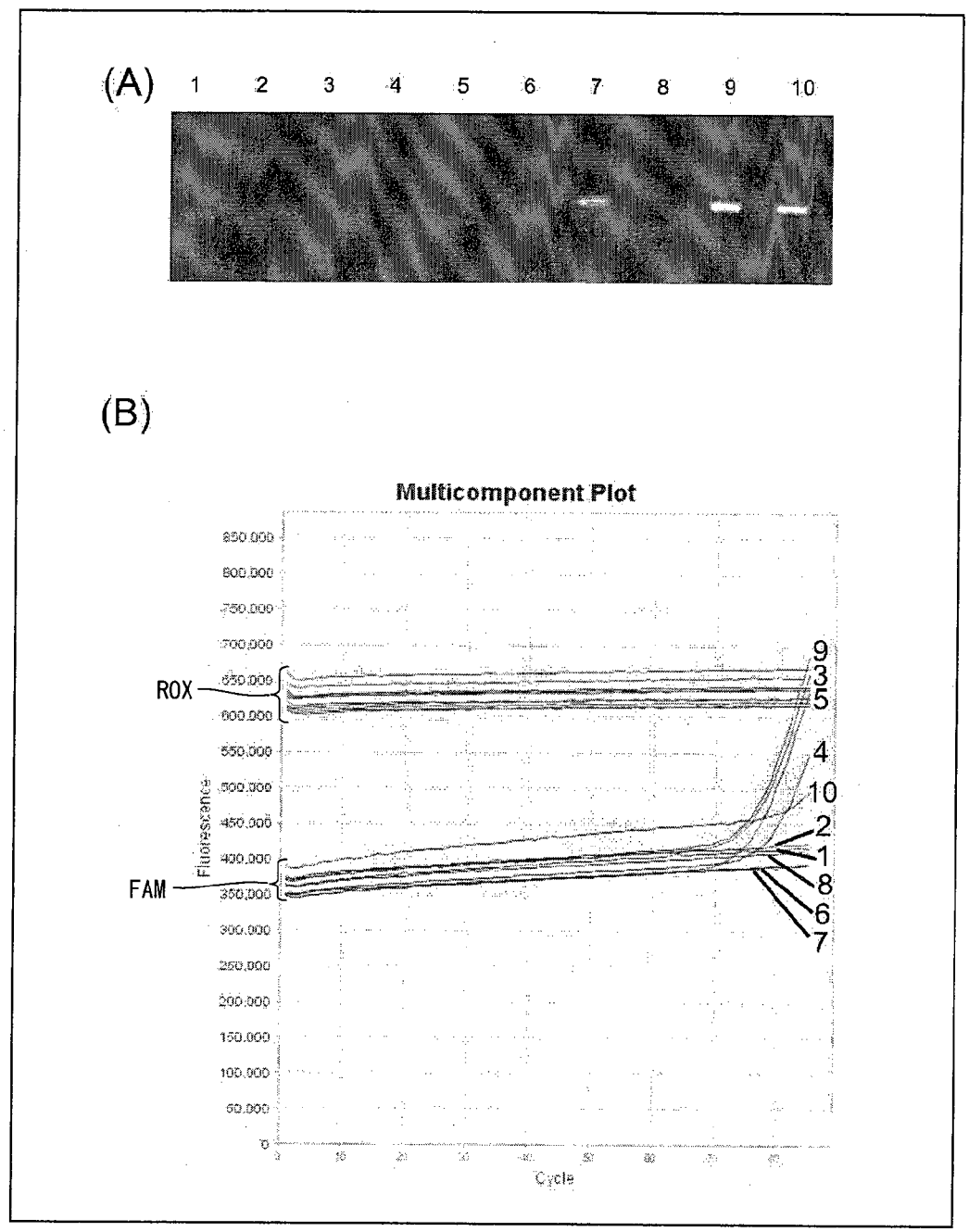

FIG. 5 relates to comparison of the sensitivity of BLV-CoCoMo-qPCR and nested-PCR.

Ten samples containing 0.7 copies of pBLV-LTR/SK were amplified by nested PCR (A) and real-time PCR with the CoCoMo 6 and CoCoMo 81 primer set (B). The 168-bp band was used to detect BLV-LTR amplicons (A). Carboxy-X-rhodamine (ROX) intensities were used for corrections of tube differences, and carboxyfluorescein (FAM) intensities were used to detect BLV-LTR amplicons (B).

Figure 6:
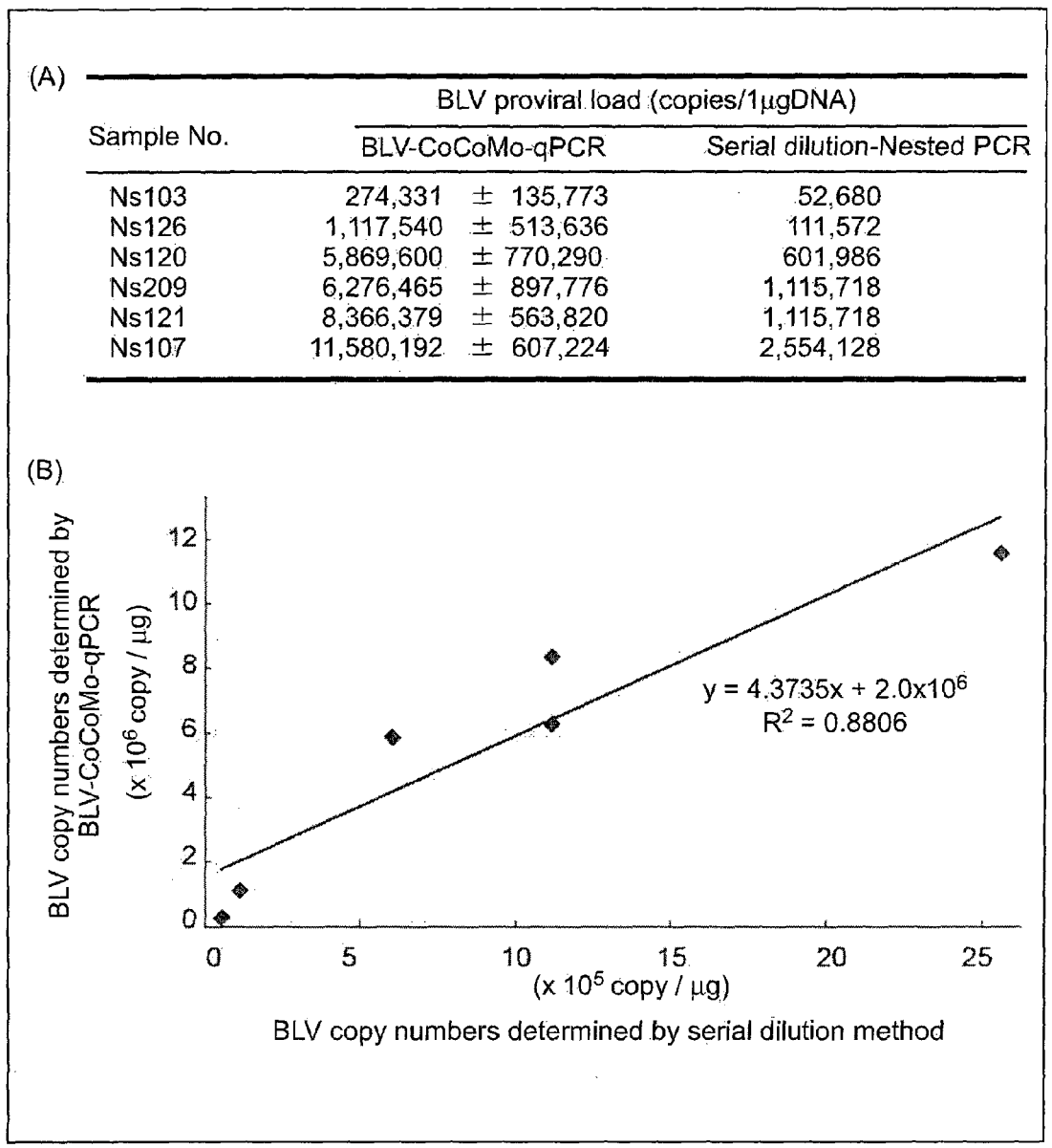

FIG. 6 relates to correlation between proviral load calculated by BLV-CoCoMo-qPCR and serial dilution-nested PCR.

(A) BLV proviral copy numbers for 1 μg of genomic DNA from 6 BLV-infected cattle were determined by BLV-CoCoMo-qPCR and serial dilution-nested PCR. For serial dilution-nested PCR, the 6 genomic DNAs were analyzed by serial tenfold dilution and subjected to nested PCR for detection of the BLV-LTR gene. Nested PCR reactions were repeated 10 times and proviral load was calculated according to a Poisson distribution model as shown in Methods. Values represent the mean+standard deviation (SD) of results from four independent experiments. (B) Scatter chart is indicated the correlation between BLV copy numbers which were determined by BLV-CoCoMo-qPCR and by serial dilution-nested PCR.

Figure 7:
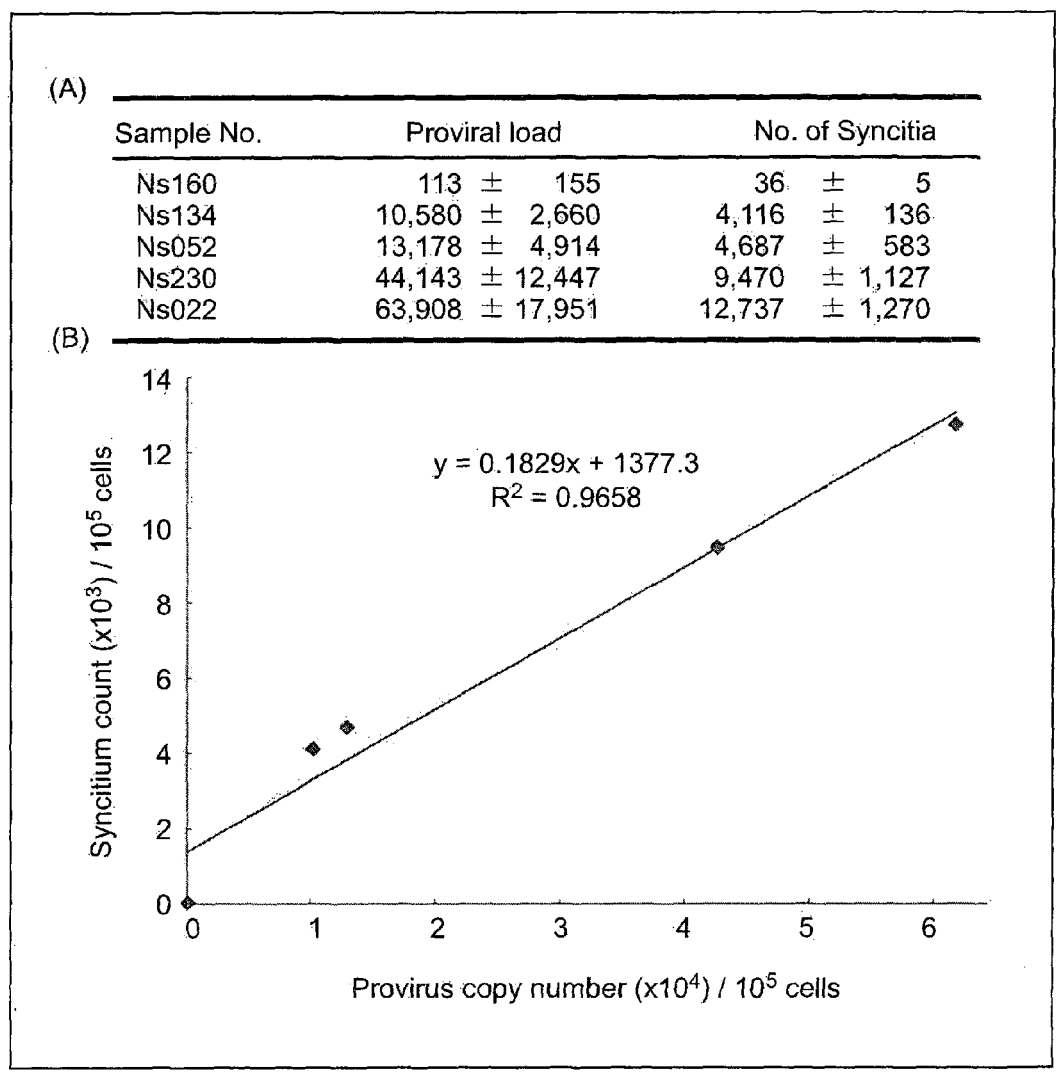

FIG. 7 relates to correlation between proviral load calculated by BLV-CoCoMo-qPCR and syncytium formation. (A) Using BLV-CoCoMo-qPCR, the proviral loads from five BLV-infected cattle were calculated and shown as provirus copy number per $1\times10^5$ cells. A syncytium formation assay using CC81 indicator cells was used to count the number of syncytia per $1\times10^5$ peripheral blood mononuclear cells (PBMCs) from five BLV-infected cattle. Values represent the mean+standard deviation (SD) of results from three samples. (B) Scatter chart is indicated the correlation between BLV copy numbers which were determined by BLV-CoCoMo-qPCR and the number of syncytia.

FIG. 8 relates to alignment of BLV LTR nucleotide sequences in samples that were positive by BLV-CoCoMo-qPCR but negative by nested-PCR.

BLV LTR sequences from 9 BLV-infected cattle were amplified by PCR using three primer pairs, BLTR56F and CoCoMo81, BLTR134F and BLTR544R, and CoCoMo6 and CoCoMo81, followed by sequencing of the PCR products. Closed arrows indicate the position, orientation and length of these primers. The LTR sequences at nucleotide positions 74-283 and 154-526 from YA40, M085 and YA35 were amplified using two primer pairs BLTR56F and CoCoMo81, and BLTR134F and BLTR544R, respectively. The LTR sequence at nucleotide positions 74-283 from YA56 was amplified by primer pair BLTR56F and CoCoMo81. The LTR sequences at nucleotide positions 166-283 from HY2, Ns27, ME10 and C336 were amplified by the primer pair CoCoMo6 and CoCoMo81. The LTR sequence at nucleotide positions 154-526 from Ns29 was amplified by primer pair BLTR134F and BLTR544R. Open arrows indicate the position, orientation and length of first primer pair, BLTR-YR and BLTRR, and the second primer pair, BLTR256 and BLTR453, for nested PCR. The numbers at the top of the sequences indicate the terminal bases according to the nucleotide sequence of the FLK-BLV subclone pBLV913 [DDBJ: EF600696]. Conserved sequences are indicated by a dot (•), deletions are indicated by a hyphen (-). A lack of sequence information is indicated by the symbol (*).

Figure 9:
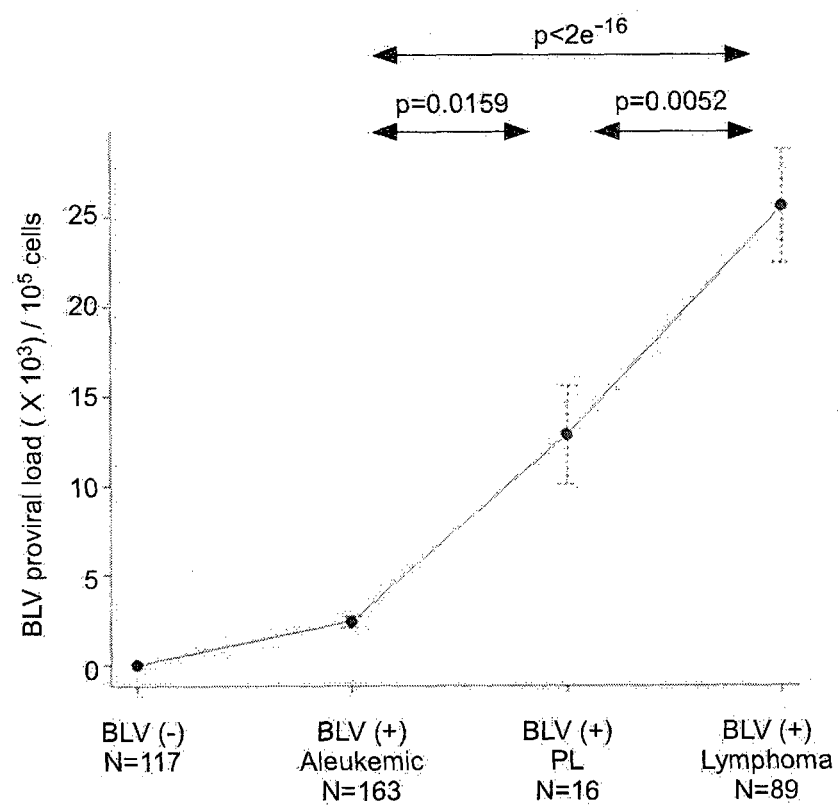

FIG. 9 relates to increased proviral load correlates with disease progression in BLV-induced enzootic bovine leukosis (EBL).

The proviral load was calculated for 385 cattle by BLV-CoCoMo-qPCR. The cattle were classified into four disease stages according to diagnosis based on previously established criteria [Non-Patent Literature 41], the genomic integration of BLV, and the detection of antibodies to BLV: 117 BLV-negative cattle (BLV-); 163 BLV-infected cattle that were clinically and hematologically normal (aleukemic); 16 clinically normal, BLV-infected cattle with persistent lymphocytosis (PL); and 89 BLV-infected cattle with lymphoma. The circles/dots indicate the average proviral load detected in each stage, and the bar indicates the standard error. P-values were calculated by pairwise t-test using R version 2.10.1 (The R Foundation for Statistical Computing).

DESCRIPTION OF EMBODIMENTS

The following will describe an embodiment of the present invention in detail.

(1. Kit for Detecting BLV)
(Basic Arrangement of Kit)

A kit for detecting bovine leukemia virus (BLV) according to the present invention is capable of selectively amplifying, through polymerase chain reaction (PCR), a DNA fragment derived from BLV. Herein, the wording "capable of selectively amplifying" means that, in the case where PCR amplifications are performed with use of the kit, DNA fragments derived from BLV can be mainly obtained as an amplification product, however, a relatively few DNA fragments derived from cattle itself and a relatively few DNA fragments derived from viruses other than BLV can be obtained (or DNA fragments derived from cattle itself and DNA fragments derived from viruses other than BLV are almost not obtained) as an amplification product.

The kit according to the present invention includes a primer set including a first PCR primer and a second PCR primer. Specifically, the primer set is one of the following (1) and (2):

(1) Combination of a first PCR primer being oligonucleotide having 50 bases or less in which successive 20 bases or more in the base sequence denoted by SEQ ID NO: 1 is included, and a second PCR primer being oligonucleotide having 50 bases or less in which successive 20 bases or more in the base sequence denoted by SEQ ID NO: 2 is included. Note that the base sequence denoted by SEQ ID NO: 1 corresponds to the base sequence denoted by primer ID No.

6 in Table 1. Further, the base sequence denoted by SEQ ID NO: 2 corresponds to the base sequence denoted by primer ID No. 81 in Table 1.

(2) Combination of a first PCR primer having 40 bases or less in which successive 20 bases or more and 25 or less in the base sequence denoted by SEQ ID NO: 1 is included, and a second PCR primer having 40 bases or less in which successive 20 bases or more and 25 or less in the base sequence denoted by SEQ ID NO: 2 is included.

Note that, even in any case of (1) and (2), lengths of the first PCR primer and the second PCR primer may be 35 bases or less, or may also be 30 bases or less. The first PCR primer preferably has the whole 25 bases denoted by SEQ ID NO: 1. The second PCR primer preferably has the whole 25 bases denoted by SEQ ID NO: 2.

The first PCR primer and the second PCR primer can include a base sequence which is not determined by SEQ ID NO: 1 or 2. For example, in the case where the PCR primer is oligonucleotide having 50 bases and only successive 20 bases are determined by the SEQ ID NO: 1, the rest 30 bases are not determined by the SEQ ID NO: 1. Even in this case, a person in the art can easily determine the rest 30 bases on the basis of at least one well-known BLV base sequence as the reference sequence, so that the rest 30 bases form a base sequence(s) hybridizable with the reference sequence.

Further, in the present invention, base R(r) indicates A (adenine) or G (guanine). Base Y(y) indicates C (cytosine) or T (thymine). Base W(w) indicates A or T. Base S(s) indicates G or C. Base K(k) indicates G or T. Base M(m) indicates A or C. Base D(d) indicates A, G, or T. Base H(h) indicates A, C, or T. Base N(n) indicates A, C, G, or T.

The base sequence denoted by the SEQ ID NO: 1 and the base sequence denoted by the SEQ ID NO: 2 each include at least one of the aforementioned bases R, Y, W, S, K, M, D, H, and N. Hence, the first PCR primer and the second PCR primer each may be a so-called degenerate primer. The degenerate primer is formed from a plurality of kinds of primers in which different kinds of bases are designated at a position of at least one of the bases R, Y, W, S, K, M, D, H, and N. The first PCR primer and the second PCR primer may be both degenerate primers each of which is a mixtures of all the possible primers (primer mix) in order to detect more kinds of BLV. However, the first PCR primer and the second PCR primer may each be one primer among the degenerate primers (primer mix).

The first PCR primer and the second PCR primer can be synthesized by a standard method known in the art of synthesizing nucleic acid.

(Other Components that May be Included in Kit)

To enhance the specificity and sensitivity of the assay, the kit for detecting BLV may further include a TaqMan™ probe that hybridizes specifically with a gene fragment amplified by the first PCR primer and the second PCR primer. For example, the TaqMan™ probe may be oligonucleotide which includes one of the base sequences denoted by SEQ ID NOs: 3 and 4.

In the Example, FAM-BLV probe (5'-FAM-CTCA-GCTCTCGGTCC-NFQ-MGB-3' (SEQ ID NO:4)) were used as the TaqMan™ probe in order to detect the PCR product of BLV-LTR in CoCoMo-qPCR. Moreover, another TaqMan™ probe (5'-FAM-CTCAGCTCTCGGTC-NFQ-MGB-3' (SEQ ID NO:3)) can be also used for detecting CoCoMo-qPCR amplicon. However the longer-primer (the former) is preferable to the short-primer in terms of sensitivity.

In order to normalize an amount of genomic DNA in a test sample by quantitatively measuring how many cells are included in the test sample, the kit for detecting BLV may further include a PCR primer set for specifically amplifying a fragment of BoLA-DRA gene (bovine leukocyte antigen DRA gene) as a single-copy host gene.

Further, the kit for detecting BLV may further include at least one of the followings as necessary: (1) various kinds of reagents and tools necessary for PCR (polymerase, PCR buffer, dNTPs, pipette, etc.), (2) various kinds of reagents and tools for preparing a sample containing DNA which is to be subjected to PCR (test tube, buffer, etc.), (3) various kinds of reagents and tools for analyzing a PCR amplified fragment (electrophoresis gel material, pipette, etc.), (4) an instruction manual for the kit, and the like.

The kit for detecting BLV according to the present invention can detect whether or not the BLV is present and/or the amount of BLV (quantification of BLV).

(2. Method for Detecting BLV)

A method for detecting BLV according to the present invention includes an amplifying step of amplifying a gene fragment, which gene fragment is derived from BLV, in a test sample with use of a kit for detecting BLV according to the present invention, the test sample having been obtained from cattle (i.e., a cow or cows).

More specifically, the method for detecting BLV according to the present invention includes steps of:

(a) a sample preparing step of preparing, from cattle, a test sample containing DNA;

(b) an amplifying step of performing polymerase chain reaction on the test sample with use of a first primer and a second primer included in the kit; and (c) a detecting step of detecting whether or not a fragment is present and/or an amount of the fragment which fragment is obtained in the amplifying step.

Hereinafter, each step will be described.

(1) Preparing Step

The preparing step is a step of preparing a sample containing DNA from cattle to be tested. The sample containing DNA is, for example, blood, a body fluid other than blood, tissue of cattle, or the like. Note that the prepared sample containing DNA contains, in addition to DNA, various kinds of RNA, proteins, cell homogenates. Accordingly, genomic DNA may be extracted from the sample by a standard purifying method known in the art.

(2) Amplifying Step

The amplifying step is a step of performing PCR on the sample with use of a first primer and a second primer included in the kit according to the present invention. The PCR can be performed by a standard method known in the art with use of a PCR amplifying device. In the case where BLV is contained in the sample, an amplifying fragment corresponding to LTRs of the BLV can be obtained. More specifically, the amplifying fragment corresponding to the LTRs of the proviral BLV integrated in genomic DNA of cattle to be tested, can be obtained.

While conditions of PCR are not particularly limited, preferable but non-limiting conditions of PCR are described below. Note that PCR exerts a synergic effects by any combinations of the following conditions 1) to 5).

1) the first primer and the second primer are degenerate primers at a concentration ratio (in a reaction solution of PCR) of the first primer to the second primer preferably in a range from 7:1 to 13:1, more preferably from 8:1 to 12:1, much more preferably from 9:1 to 11:1, and most preferably 10:1.

2) a final concentration of genomic DNA contained in the reaction solution of PCR is preferably ranged from 1 ng/μl to 100 ng/μl, more preferably from 1.5 ng/μl to 20 ng/μl.

Herein, a final concentration of the first primer that is a degenerate primer is preferably ranged from 400 nM to 600 nM, and more preferably from 450 nM to 550 nM. Further, a final concentration of the second primer that is a degenerate primer is preferably ranged from 40 nM to 60 nM, and more preferably from 45 nM to 55 nM.

3) the number of cycles of PCR is preferably ranged from about 30 times to 100 times, and more preferably from about 60 times to 90 times, and most preferably from about 80 times to 90 times.

4) annealing temperature of PCR is preferably ranged from 55° C. to 70° C., more preferably from 55° C. to 65° C., and most preferably about 60° C.

5) a concentration of magnesium chloride contained in the reaction solution of PCR is preferably ranged from 2.5 mM to 3.5 mM, more preferably 2.8 mM to 3.2 mM, and most preferably about 3 mM.

Note that, in the case where the kit according to the present invention includes a PCR primer set for specifically amplifying a fragment of BoLA-DRA gene (bovine leukocyte antigen DRA gene), PCR with use of this PCR primer set can be performed in the same reaction system as that with use of a set of the first and second primers.

Further, the PCR amplification can be also performed as a so-called real-time PCR.

(3) Detecting Step

The detecting step is a step of detecting presence or absence of the PCR amplifying fragment and/or an amount of the PCR amplifying fragment which the PCR amplifying fragment is obtained in the amplifying step. The presence or absence of the PCR amplifying fragment (amplicon) can be checked by a standard method known in the art. For example, the detecting step may be performed by electrophoresis so that the presence or absence, the amount, and a size of the PCR amplifying fragment can be analyzed Further, in the case where the kit according to the present invention includes a TaqMan™ probe that specifically hybridizes with a gene fragment amplified by the first PCR primer and the second PCR primer, the kit can detect presence or absence and the amount of the PCR amplifying fragment with a fluorescent signal.

If the detection of the PCR amplifying fragment shows that the PCR amplifying fragment exists, it is determined that BLV exists in the sample. Further, if the detection of the PCR amplifying fragment shows that the PCR amplifying fragment does not substantially exist, it is determined that BLV does not exist in the sample. That is, whether the cattle have BLV or not can be diagnosed by performing the detecting step.

As shown in the Example, this assay is highly specific, sensitive, quantitative and reproducible, and was able to detect BLV in a number of samples that were negative using the previously developed nested-PCR assay. The assay was also highly effective in detecting BLV in cattle from a range of international locations. And also, this assay enabled us to demonstrate that proviral load correlates not only with BLV infection capacity as assessed by syncytium formation, but also with BLV disease progression.

Example

The following will further specifically describe the present invention with reference to Examples, Comparative Examples, etc. below. However, the present invention is not limited to these.

Results

Figure 1:
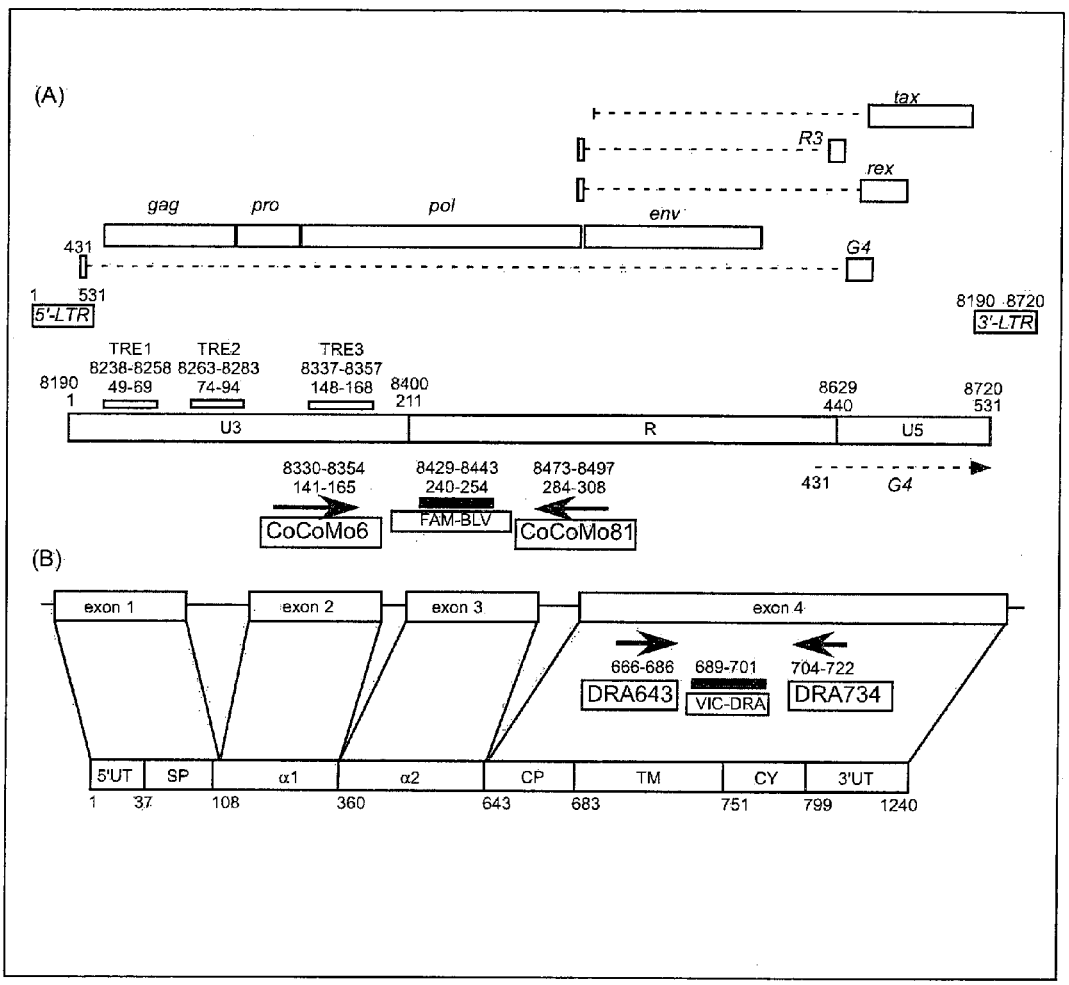
FIG. 1 relates to the position, length and orientation of primers and probes used in the bovine leukemia virus (BLV)-CoCoMo-qPCR method.

Principle of Absolute Quantification for Determination Of BLV Proviral Copy Number To determine the absolute copy number of BLV provirus, we selected the LTR region as a target sequence for PCR amplification ((A) in FIG. 1). In designing the assay, we took into account the fact that two LTRs will be detected for each individual BLV genome (see equation below). To normalize genomic DNA input, the assay also included a parallel amplification of the single-copy BoLA-DRA gene ((B) in FIG. 1). The number of proviral copies per 100,000 cells is calculated according to the following equation:

BLV provirus load=BLV provirus copy number/diploid cell number×100,000 cells=(BLV-LTR copy number/2)/(BoLA-DRA copy number/2)×100,000 cells       (A)

Use of the CoCoMo Algorithm to Construct a Primer Set with the Ability to Amplify all BLV Strains To amplify all BLV variants, primers targeting the BLV LTR region were constructed using the modified CoCoMo algorithm, which was developed to design PCR primers capable of amplifying multiple strains of virus. We collected 356 BLV nucleotide sequences from GenBank (on 30 Apr. 2009). From these BLV sequences, 102 LTR sequences were selected according to GenBank annotations. From the LTR sequences, we selected 85 sequences that were large enough to determine homologies and assigned the sequences to major BLV-LTR groups based on homology using a graphical approach with Pajek graphical software. 52 of these sequences were selected for primer design. The target sequences were subjected to a BLV-LTR modified version of the CoCoMo-primer-design algorithm, which was developed for designing degenerate primers to detect multiple strains of virus. Using these sequences as templates, a total of 72 primer sets ((B) in FIG. 2) with 49 candidate primers (Table 1) were designed.

Selection of the Primer Set and Probe for Amplification of the BLV-LTR Region

To determine whether the CoCoMo primer sets amplified the BLV LTR region, touch-down PCR was performed with 72 candidate primer sets ((B) in FIG. 2) using genomic DNA extracted from BLV-infected BLSC-KU-17 cells. As shown in (A) in FIG. 2, we identified 16 sets of primers, 1-6, 9, 15-17, 20, 21, 24, 33, 43 and 46, which successfully amplified the BLV LTR region.

The specificity of the 16 selected primer sets was evaluated by melting-curve analysis of amplification using genomic DNA extracted from BLSC-KU-17 cells or PBMCs from BLV-free normal cattle Ns118, with reagent-only as the negative control. (C) in FIG. 2 shows the four typical melting-curves. Amplicons consisting of a single PCR product with a single melting temperature exhibited a single peak, while amplicons consisting of two or more products exhibited multiple peaks. The amplicon generated using primer set ID15 of CoCoMo 6 and CoCoMo 81 had a single melting temperature using BLSC-KU-17 genomic DNA. Using these primers, no amplicons were generated using genomic DNA from PBMCs in BLV-free normal cattle Ns118 or using the reagent-only control. In contrast, other primer sets, such as ID3, ID16 and ID17 generated amplicons from genomic DNA extracted from PBMCs from BLV-free normal cattle Ns118 or in reagent only, as well as from genomic DNA extracted from BLSC-KU-17 cells. Therefore, we proceeded to optimize the amplification conditions using primer sets CoCoMo 6 and CoCoMo 81, which were the best pair for the detection of the BLV-LTR region ((D) in FIG. 2). Under these optimized conditions, amplification melting-curve analysis using genomic DNAs extracted from 56 BLV-infected cattle and from 3 BLV-free normal cattle showed the same patterns as seen in BLSC-KU-17 cells and BLV-free normal cattle Ns118 (data not shown).

The internal BLV TaqMan™ probe was constructed from a region of low variability located between positions corresponding to the CoCoMo 6 and CoCoMo 81 primers in the LTR regions of the BLV genome (FIG. 1), and was labeled with carboxyfluorescein (FAM) dye, non-fluorescent quencher (NFQ) and minor groove binder (MGB) probe for enhancing the probe melting temperature. The probe was designated as FAM-BLV.

Alignment of the sequences corresponding to the primer and probe regions from the 52 BLV LTR sequences taken from GenBank are shown in FIG. 3. Based on this comparison, out of the 52 sequences, 8 individual sequences corresponding to CoCoMo 6 primer and 4 individual sequences for CoCoMo 81 primer could be arranged. The alignment demonstrated that although the sequences in the probe region were sufficiently conserved to allow alignment of the BLV variants, the sequences corresponding to the CoCoMo 6 and CoCoMo 81 primers exhibited a low degree of similarity.

Construction of the Primer Set and Probe for Quantification of the BoLA-DRA Gene For normalization of the genomic DNA used as the PCR template, we designed primers and a probe for quantification of the BoLA-DRA gene (FIG. 1). We obtained sequences from an MR1 cDNA clone [DDBJ: No. D37956] and selected the exon 4 region of the BoLA-DRA gene as the target for amplification. We designed the amplification primer set DRA643 and DRA734 and the internal BoLA-DRA TaqMan™ probe using the Primer Express 3.0 (Applied Biosystems, Tokyo, Japan). The probe was labeled with VIC dye, NFQ and an MGB probe for enhancing the probe melting temperature, and was designated as VIC-DRA.

Quantification of Plasmid DNA Copy Number to Create Standard Curves for Absolute Quantitative PCR To obtain standards for quantification of BLV proviral DNA and cellular DNA, pBLV-LTR/SK, which includes a full-length LTR of BLV, and pBoLA-DRA/SK, which includes a full-length bovine DRA gene, were prepared at 103.1 ng/µl (pBLV-LTR$^{conc}$) and 125.0 ng/µl (pBoLA-DRA$^{conc}$), respectively. The copy numbers of these plasmids were calculated by the serial dilution method: each plasmid was diluted 10-fold and the target DNA was detected by nested PCR. For example, at a $10^{-11}$ dilution of pBLV-LTR$^{conc}$, PCR amplification failed to detect any PCR product, including the BLV LTR. The PCR reaction was then replicated 10 times at the $10^{-11}$ dilution, and the success rate was found to be 5/10. This result showed that 5 of 10 PCR solutions did not contain the LTR gene, expressed in equation form as: f (x=0)=5/10. Finally, the average copy number of the target gene (A) was calculated as $-\log_e(5/10)=0.231$ corresponding to a copy number for pBLV-LTR$^{conc}$ of 2.31× $10^{10}$/µl. Using the same strategy, the copy number of pBoLA-DRA$^{conc}$ was determined to be 2.54×$10^{10}$/µl. For confirmation of the reliability of estimated copy numbers, we also calculated draft copy numbers from the DNA weight and obtained a very similar result (2.35×$10^{10}$ for pBLV-LTR$^{conc}$, and 2.85×$10^{10}$ for pBoLA-DRA$^{conc}$).

Final Procedure for the Optimization of BLV-CoCoMo-qPCR

To construct the standard curve, the following dilutions of pBLV-LTR$^{conc}$ and pBoLA-DRA$^{conc}$ were created: 0.1 copy/ µl, 1 copy/µl, 1,000 copies/µl and 1,000,000 copies/µl. A 168-bp amplicon from the BLV-LTR region was amplified in a total volume of 20 µl of 1× TaqMan Gene Expression Master Mix containing 500 nM CoCoMo 6 primer, 50 nM CoCoMo 81 primer, 150 nM FAM-BLV probe (5'-FAM-CTCAGCTCTCGGTCC-NFQ-MGB-3' (SEQ ID NO:4)), and 30 ng of template DNA. In addition, a 57-bp amplicon of the BoLA-DRA region was amplified in a total volume of 20 µl of 1× TaqMan Gene Expression Master Mix containing 50 nM of DRA643 primer (5'-CCCAGAGACCACAGA-GAATGC-3' (SEQ ID NO:5)), 50 nM of DRA734 (5'-CCCACCAGAGCCACAATCA-3' (SEQ ID NO:6)) primer, 150 nM of VIC-DRA probe (5'-VIC-TGTGTGC-CCTGGGC-NFQ-MGB 3' (SEQ ID NO:7)), and 30 ng of template DNA. PCR amplification was performed with the ABI 7500 Fast Real-time PCR system according to the following program: Uracil-DNA Glycosylase (UDG) enzyme activation at 50° C. for 2 min followed by AmpliTaq Gold Ultra Pure (UP) enzyme activation at 95° C. for 10 min, and then 85 cycles of 15 s at 95° C. and 1 min at 60° C. Copy numbers obtained for the BLV-LTR and BoLA-DRA were used to calculate BLV proviral load per 100,000 cells, as shown in Equation (A).

Reproducibility of BLV-CoCoMo-qPCR

The intra- and inter-assay reproducibility of BLV-Co-CoMo-qPCR for determination of BLV proviral copy number was evaluated using aliquots of genomic DNA extracted from blood samples from seven BLV-infected cattle (Table 2). For determination of intra-assay reproducibility, we examined triplicate PCR amplifications from each sample, with the assay being repeated three times. A total of 21 examinations were performed and the intra-assay coefficient of variance (CV) ranged from 0% to 20.5% (mean 8.6%). For determination of inter-assay reproducibility, we performed three independent experiments for each sample. The values for the inter-assay CV for BLV proviral copy number per 100,000 cells ranged from 5.5% to 19.8% (mean 12.7%). These results clearly demonstrated that this assay has good intra- and inter-assay reproducibility.

Evaluation of the Specificity of BLV-CoCoMo-qPCR Primers Using Various Retroviruses The specificity of BLV-CoCoMo-qPCR primers was tested using various retroviral molecular clones, including BLV, HTLV-1, human immunodeficiency virus type 1 (HIV-1), simian immunodeficiency virus (SIV), mouse mammary tumor virus (MMTV), Molony murine leukemia virus (M-MLV), and a range of plasmids including pUC18, pUC19, pBR322, and pBluescript II SK (+). For real-time PCR, CoCoMo 6 and CoCoMo 81 primers were used with 0.3 ng of each plasmid, and the products were analyzed by 3% agarose-gel electrophoresis. A single PCR product, 168-bp in length, was observed only for the BLV infectious molecular clone ((A) in FIG. 4), with a copy number of 7.9×$10^{10}$/µg+4.3×$10^{10}$/µg ((B) in FIG. 4). No amplicons were detected for any of the other plasmids. These results strongly indicate that BLV-CoCoMo-qPCR primers specifically amplify the BLV LTR without amplifying the LTRs of other retroviruses.

Evaluation of the Sensitivity of BLV-CoCoMo-qPCR Compared with Nested PCR

To determine the sensitivity of BLV-CoCoMo-qPCR, 20 solutions, each containing 0.7 copies of pBLV-LTR/SK, were amplified by nested PCR and real-time PCR using the CoCoMo 6 and CoCoMo 81 primer set (FIG. 5). Three out of ten nested PCR amplifications were positive, and the copy number was estimated to be 0.36. For real-time PCR using the CoCoMo 6 and CoCoMo 81 primer set, five out of ten PCR amplifications were positive, and the copy number was estimated to be 0.69. This result showed that the sensitivity of BLV-CoCoMo-qPCR was 1.9-fold greater than that of nested PCR.

Comparison of BLV-CoCoMo-qPCR and Serial Dilution-Nested PCR

The serial dilution method is effective for quantifying the copy number of a target gene. The BLV proviral copy number per 1 μg of genomic DNA was calculated for five BLV-infected cattle by serial dilution-nested PCR and real-time PCR with the CoCoMo 6 and CoCoMo 81 primer set ((A) in FIG. 6). The BLV proviral copy number obtained by both methods was confirmed by regression analysis: the square of the correlation coefficient ($R^2$) was 0.8806 ((B) in FIG. 6), indicating that the copy number obtained by real-time PCR with the CoCoMo primers correlated with that obtained by serial dilution-nested PCR. Thus, it appears that real-time PCR with the CoCoMo 6 and CoCoMo 81 primer set can be used to obtain the copy number of BLV provirus from a clinical sample.

Correlation of BLV-CoCoMo-qPCR and Syncytium Formation Assay

To test whether the BLV proviral copy number correlates with the capacity for infection with BLV, BLV-CoCoMo-qPCR and a syncytium formation assay were conducted on samples from five BLV-infected cattle. We evaluated the capacity for transmission of BLV by coculturing $1\times10^5$ PBMCs from five BLV-infected cattle with inducer CC81 cells for three days and comparing proviral copy numbers with $1\times10^5$ cells from the same cattle ((A) in FIG. 7). Proviral copy numbers ranged from 113 to 63,908 copies per $10^5$ cells, and syncytium numbers ranged from 36 to 12,737 per $10^5$ PBMCs. Regression analysis for these samples revealed that the level of provirus load positively correlated with the number of syncytia ($R^2=0.9658$), as shown in (B) in FIG. 7.

BLV Provirus Detection in Cattle from Different Geographic Locations by BLV-CoCoMo-qPCR and Nested PCR BLV-CoCoMo-qPCR has the potential ability to detect various BLV strains, both known and unknown, because degenerate primers are capable of detecting highly degenerate sequences. In the experiments described above, we found that the sensitivity of BLV-CoCoMo-qPCR was greater than that of nested PCR. Therefore, we examined whether BLV-CoCoMo-qPCR can detect BLV provirus in cattle from different geographic locations worldwide. We tested 54 cattle from one farm in Japan, 15 cattle from two farms in Peru, 60 cattle from four farms in Bolivia, 32 cattle from three farms in Chile and 5 cattle from one farm in the U.S.A., and compared the results obtained by BLV-CoCoMo-qPCR with the results obtained by nested PCR (Table 3). The amplification of BLV LTR by the two methods divided the 166 cattle into three groups. The first group of cattle (n=107) was positive for BLV LTR by both methods (50 in Japan, 7 in Peru, 27 in Bolivia, 18 in Chile, and 5 in U.S.A.). The second group of cattle (n=50) was negative for BLV LTR by both methods (2 in Japan, 7 in Peru, 28 in Bolivia, and 13 in Chile). The third group of cattle (n=9) was positive by BLV-CoCoMo-qPCR but negative by nested-PCR (2 in Japan, 1 in Peru, 5 in Bolivia, and 1 in Chile). Interestingly, none of the cattle were negative by BLV-CoCoMo-qPCR but positive by nested-PCR. Thus, the nested-PCR and BLV-CoCoMo-qPCR methods gave the same result for 94.6% of the cattle tested, but for 5.4% of the cattle, only the CoCoMo-qPCR was able to detect BLV provirus. These results clearly showed that the sensitivity of BLV-CoCoMo-qPCR was higher than that of nested-PCR.

As shown in Table 3, we detected several samples that were positive by BLV-CoCoMo-qPCR but negative by nested-PCR. To confirm that these samples were infected with BLV, and to investigate why these samples were not detected by nested PCR, we sequenced the LTR region of nine samples from this group: YA40, MO85, YA35, YA56 and ME10 from Bolivia, HY2 from Peru, C336 from Chile, and Ns27 and Ns29 from Japan. We were able to detect BLV-LTR sequences in all nine samples (FIG. 8), thus confirming the high specificity of BLV-CoCoMo-qPCR. In two of the nine samples, we identified mismatch sequences at the annealing region for the primer BLTR453, which was used for amplification of the LTR in nested-PCR. This is a possible explanation for why the nested PCR failed to detect the BLV provirus.

Correlation Analysis of Disease Progression and BLV Proviral Load

To characterize differences in BLV proviral load in the early and late stages of disease, we calculated BLV proviral copy numbers for 268 BLV-infected cattle in different stages of progression of EBL. We measured proviral load in 163 BLV-positive, healthy cattle, 16 BLV-infected cattle with PL, 89 BLV-infected cattle with lymphoma, and 117 BLV-free normal cattle by BLV-CoCoMo-qPCR (FIG. 9). The proviral loads were significantly increased at the PL stage compared with the aleukemic stage (p=0.0159) and were further increased at the lymphoma stage (p=0.0052). No BLV was detected in the 117 BLV-free normal cattle. Thus, we were able to demonstrate that BLV proviral copy number increased with increasing severity of disease.

DISCUSSION

In this study, we describe the successful development of a highly specific, accurate, and sensitive method for the quantification of BLV proviral load from infected animals.

The BLV-CoCoMo-qPCR system is able to detect various BLV strains from a broad geographical origin, including Japan, Peru, Bolivia, Chile and the U.S.A. Although early studies on genetic variability of the BLV env gene identified very little variation among isolates [Non-Patent Literature 28], recent studies based on restriction fragment length polymorphism analysis and on analysis of the full-length BLV env gene have revealed at least seven different BLV genotypes in circulation worldwide [Non-Patent Literatures 24, 27, 29]. This novel classification suggests that BLV divergence has increased worldwide. From a total of 356 BLV sequences in GenBank, we were able to obtain 52 distinct BLV LTR nucleotide sequences. This indicates that many BLV variants exist and our results suggest that detection of all of these variants is possible using BLV-CoCoMo-qPCR. Thus, we have clearly demonstrated that the CoCoMo algorithm is a useful tool for designing degenerate primers corresponding to multiple BLV variants. In fact, Tong et al. [Non-Patent Literature 30] indicated that semi-nested or nested PCR assays with consensus-degenerate hybrid oligonucleotide primers for Paramyxoviridae could be developed to be either highly specific or more broadly inclusive, enabling targeting at the subfamily or genus level. Using this type of approach, there is a risk that the degeneracy of the CoCoMo primers could be too high, thereby reducing the concentration of primer specific to the target sequence and decreasing the assay's sensitivity. This issue did not arise in our study since BLV-CoCoMo-qPCR was highly sensitive and gave superior results to nested-PCR amplification (FIG. 6). In addition, the BLV-CoCoMo-qPCR system was very effective in detecting virus in BLV-infected cattle from a range of geographic locations (Table 3). The TaqMan™ probe was used to improve sensitivity and specificity and acts to counter any drawbacks associated with high degeneracy. It is important to note that the sequence of the BLV TaqMan™ probe, located between positions corresponding to the CoCoMo 6 and CoCoMo 81 primers, was completely conserved among the 52 BLV variants. The ELISA and immunodiffusion screening methods for BLV in cattle are also highly sensitive but they act by detecting antibodies against BLV, in contrast to the direct detection of integrated provirus by PCR [Non-Patent Literature 17]. The ELISA and immunodiffusion methods suffer from a high rate of false positives and they are also ineffective in determining whether calves are infected since circulating maternal antibodies from BLV-infected dams can interfere with the assay. Reliable detection of BLV-infection in cattle therefore requires a high-sensitivity method for the detection of provirus. To this end, we developed BLV-CoCoMo-qPCR.

Several approaches were used to confirm the high specificity of BLV quantification using CoCoMo primers. First, the CoCoMo 6 and CoCoMo 81 primers yielded a single peak by melting curve analysis in cells infected with BLV but did not amplify a product in uninfected cells or in the reagent-only negative control. Second, PCR amplification was detected in BLV-positive cattle but was negative in all 120 BLV-negative cattle tested. Third, infectious molecular clones including several non-BLV retroviral LTRs were not amplified by our system.

A previous study [Non-Patent Literature 31] reported a method to quantify BLV provirus using real-time PCR. This method targeted the BLV env and pol genes, which are present at only one copy per provirus, and the primer annealing regions were potentially susceptible to mutation. The BLV-LTR target of CoCoMo-qPCR is present at two copies per provirus, which contributes to the improved sensitivity of our assay. Indeed, using the qPCR method described by Lew et al. [Non-Patent Literature 31], we could not detect provirus at less than 18 copies/$10^5$ cells, a concentration that was readily detectable by CoCoMo-qPCR (data not shown). Our method also has the advantage that the use of degenerate primers allows for the detection of BLV sequence variants, including those that arise from mutations.

The BLV-CoCoMo-qPCR method was also accurate. The provirus copy number obtained using real-time PCR with CoCoMo primers correlated closely with the result from serial dilution-nested PCR. Because we aimed to use BLV-CoCoMo-qPCR to quantify cell-associated BLV provirus, we performed a parallel quantitation of the single-copy cellular gene BoLA-DRA. This measurement allowed adjustment for variations in amplification efficiency between samples. Using this strategy, we observed sufficient intra- and inter-assay reproducibility for the diagnosis of infected animals. The assay CV range was 0.0% to 20.5%, which was markedly better than that reported for quantification of HTLV-1 proviral load (8.2% to 31.4% [Non-Patent Literature 32] or 49% to 55% [Non-Patent Literature 33]). The high reproducibility of our assay enabled its use for the quantitation of proviral load during disease progression. The accuracy of CoCoMo-qPCR was also confirmed by sequencing analysis. We selected nine samples in which BLV provirus could be detected by CoCoMo-qPCR, but not by nested PCR, and sequenced the amplicons. Using this strategy, we confirmed that the nine samples were infected by BLV, and this highlights the ability of the CoCoMo-qPCR method to detect provirus in samples that were negative by nested PCR. In two of the nine samples, sequence mismatches were detected at the annealing region for the nested PCR primers, thereby suggesting an explanation for the failure of nested-PCR to detect BLV in these samples.

The syncytia assay is a common strategy for detecting viable BLV virus particles [Non-Patent Literature 34]. However, this method requires cell culture, is time consuming and often difficult, and also has low sensitivity. We tested whether the proviral copy number obtained with our assay correlated with the syncytium formation assay, since this would suggest that our assay could be used for diagnosis at the BLV infection stage. Syncytia formation correlated strongly with a proviral load of over 10,000 copies/$10^5$ cells, as calculated by BLV-CoCoMo-qPCR. In BLV-infected cattle with a low proviral load detected by BLV-CoCoMo-qPCR, syncytia formation could hardly be detected. Thus, BLV-CoCoMo-qPCR appears to be capable of correctly determining the level of BLV infection in animals with low viral loads.

The pre-leukemic phase of BLV infection, called PL, is characterized by the expansion of infected surface immunoglobulin M-positive B-cells with proviral insertion at multiple sites. On the other hand, a unique integration site is characteristic of malignant of malignant B-cells found in BLV-infected individuals after the onset of overt leukemia/lymphoma [Non-Patent Literatures 13, 23, 35]. According to this model, proviral load should increase during disease progression but this has not been formally demonstrated. Using BLV-CoCoMo-qPCR, we were able to detect an increase in proviral load during disease progression. This result strongly suggests that proviral load may be an excellent indicator for monitoring the progression of disease but may also be useful for implementing segregation programs to minimize BLV transmission. Previous experiments also identified host factors or genetic backgrounds that correlate with disease progression. For example, tumor-associated c143 antigens have been identified that are serine phosphorylated specifically in cattle with EBL, and genetic polymorphisms in cancer-associated genes such as p53 and tumor necrosis factor (TNF) have also been linked with EBL [Non-Patent Literatures 35-41]. Proviral load may also be a valuable measure for identifying markers that influence progression to the lymphoma stage. Our assay may be valuable for estimating the effectiveness of vaccination and may also be capable of detecting changes in proviral load in BLV-infected cattle with the TNF and BoLA alleles that have previously been associated with resistance or susceptibility to BLV-induced lymphoma. Finally, since our assay detected all BLV variants, the CoCoMo algorithm appears to be a useful tool for designing degenerate primers for the quantification of proviral loads of other retroviruses, including HTLV and HIV-1.

CONCLUSIONS

Using CoCoMo primers, we have developed a new quantitative real-time PCR method to measure the proviral load of known and novel BLV variants. Our method is highly specific, sensitive, quantitative and reproducible for detection of the BLV LTR region in infected animals. The method was effective in detecting BLV in cattle from a range of geographical locations, and detected BLV in a broader range of samples than the previously developed nested-PCR. Finally, we have shown for the first time that the proviral load correlates well with the stage of disease progression.

Methods

Clinical Samples, Cell Lines and DNA Extraction

Blood samples were obtained from 117 healthy cattle with negative BLV serology, 163 BLV-infected cattle that were clinically and hematologically normal, 16 clinically normal BLV-infected cattle with PL, and 89 BLV-infected cattle with EBL. These cattle were all maintained in Japan. A further 116 cattle that were maintained in Bolivia, Peru, Chile and the U.S.A were included in the study. BLV-infected cattle were classified according to previously established criteria [Non-Patent Literature 42] and the genomic integration of the BLV provirus. PBMCs were separated from blood by the method of Miyasaka and Trnka [Non-Patent Literature 43].

The BLV-infected B lymphoma cell line BLSC-KU-17 [Non-Patent Literature 44] was maintained in Dulbecco's modified Eagle's medium (Life Technologies Japan, Tokyo, Japan) supplemented with 10% heat-inactivated fetal calf serum (FCS) (Sigma Aldrich Chemie Gmbh, Steinem, Germany), penicillin and streptomycin. CC81, a cat cell line transformed by mouse sarcoma virus, was maintained in RPMI 1640 medium (Sigma-Aldrich Co. Ltd., Ayrshire, UK) supplemented with 10% heat-inactivated FCS, penicillin and streptomycin.

Genomic DNA was extracted from (a) whole blood by the DNA Wizard Genomic DNA purification Kit (Promega, Madison, Wis.), (b) PBMCs by the procedure described by Hughes et al. [Non-Patent Literature 45] and (c) 40 µl of whole blood spotted on FTA elute cards (Whatman, Tokyo, Japan), using standard procedures.

Design of Primers and Probes

The 52 variants of individual BLV LTR sequences were selected from 356 BLV sequences in GenBank. The target sequences were subjected to a BLV-LTR modified version of the CoCoMo-primer-design algorithm (http://www.gene-knot.jp/cocomo; Endoh D, Mizutani T, Morikawa S Hamaguchi I, Sakai K, Takizawa K, Osa Y, Asakawa M, Kon Y, Hayashi M: CoCoMo-Primers: a web server for designing degenerate primers for virus research. Submitted), which was developed for designing degenerate primers to detect multiple strains of viruses. Note that, in order to utilize BLV sequences in which the LTR regions have not been reported officially, the 52 variants of individual BLV LTR sequences are extracted by combining a BLAST program and a cluster selection method on the basis of known LTR sequences. Further, in a case where the CoCoMo-primer-design algorithm is used, common four bases in the target sequences (two correspondent bases-one free base-two correspondent bases) are generally searched. However, common five bases are searched in the BLV herein.

To detect specific PCR products, we used the TaqMan™ probe system (Applied Biosystems, Tokyo, Japan), with probe sequences designed using Primer Express software, version 2.0 (Applied Biosystems).

(Details about the CoCoMo Algorithm)

Many viruses mutate during evolution, which can lead to alterations in pathogenicity and epidemic outbreaks [Non-Patent Literatures 1, 2]. The development of molecular techniques, especially those applications based on the polymerase chain reaction (PCR), has revolutionized the diagnosis of viral infectious diseases [Non-Patent Literatures 3, 4]. Degenerate oligonucleotide primers, which allow the amplification of several possible mutated versions of a gene, have been successfully used for cDNA cloning and for the detection of sequences that are highly variable due to a high rate of mutation [Non-Patent Literature 5]. Degenerate primers are useful for the amplification of unknown genes but also for the simultaneous amplification of similar, but not identical, genes [Non-Patent Literature 6]. The use of degenerate primers can significantly reduce the cost and time spent on viral detection. The "Coordination of Common Motifs" (CoCoMo) algorithm has been developed especially for the detection of multiple virus species (Endoh D, Mizutani T, Morikawa S, Hamaguchi I, Sakai K, Takizawa K, Osa Y, Asakawa M, Kon Y, Hayashi M: CoCoMo-Primers: a web server for designing degenerate primers for virus research, submitted). This program uses an extension of the COnsensus-DEgenerate Hybrid Oligonucleotide Primer (CodeHop) technique [Non-Patent Literature 7], which is based on multiple DNA sequence alignments using MAFFT [Non-Patent Literature 8]. The CoCoMo selects common gap tetranucleotide motifs (GTNM), which include codons from the target sequences. It then selects amplifiable sets of common GTNMs using a database-based method and constructs consensus oligonucleotides at the 5' end of each common amplifiable GTNM. The consensus degenerate sequence is then attached to the designed degenerate primers. Thus, the CoCoMo algorithm is very useful in the design of degenerate primers for highly degenerate sequences.

Plasmids

To obtain pBLV-LTR/SK, which included a full-length LTR from BLV, we used PCR with the primers BLV-LTR/XhoI (5'-CCCGCTCGAGTGTATGAAAGATCATGC-CGA-3' (SEQ ID NO:8); positions 1 to 20) and BLV-LTRR/BamHI (5'-CGGGATCCTGTTTGCCGGTCTCTCCTGG-3' (SEQ ID NO:9); positions 510 to 530) and genomic DNA extracted from KU-17 cells as a template. PCR products were cloned into pBluescript II SK (+) (Stratagene, La Jolla, Calif.). The numbering of nucleotides corresponds to positions in the sequences determined by Derse et al. [Non-Patent Literature 46]. To generate pBoLA-DRA/SK, which includes a full-length bovine DRA gene, we digested MRI from the mammalian expression vector pCDM8 [Non-Patent Literature 47] with Xba I. The Xba I-Xba I fragment including the MRI sequence was then subcloned into pBluescript II SK (+) (Stratagene). Additional clones used included a BLV infectious clone, pBLV-IF [Non-Patent Literature 34]; an HTLV-1 infectious clone, pK30 [Non-Patent Literature 48]; an HIV-1 infectious clone, pNL4-3 [Non-Patent Literature 49]; an SIV infectious clone, SIV-mac239/WT [Non-Patent Literature 50]; a hybrid MMTV provirus plasmid [Non-Patent Literature 51]; an M-MLV infectious clone, pL-4 [Non-Patent Literature 51]; and plasmids including pUC18 (Takara Bio Inc., Tokyo, Japan), pUC19 (Takara Bio Inc.), and pBR322 (Promega).

Calculation of Copy Number by the Serial Dilution Method pBLV-LTR/SK and pBoLA-DRA/SK were digested with Sca I and purified using a Sephadex G-50 column (GE Healthcare Japan, Tokyo, Japan). The genomic DNA was digested with Xho I in the presence of 5 mM spermidine for 24 h. The samples were diluted to serial ten-fold dilutions with TE buffer [10 mM Tris-HCl (pH 8.0) with 1 mM ethylenediamine tetraacetic acid (EDTA)] on-ice. To avoid DNA adsorption to the microtubes, super smooth processed tubes (BM4015 Platinum super polypropylene; BM bio, Tokyo, Japan) were used for the preparation of template for the standard curve.

Limiting dilutions were performed for linearized pBLV-LTR/SK, pBoLA-DRA/SK and genomic DNA. Detection of the BLV-LTR gene and the BoLA-DRA gene from plasmid DNA was performed by real-time PCR with the CoCoMo primers 6 and 81, or the primers DRA643 and DRA734, respectively. The BLV-LTR gene was also detected in genomic DNA using nested PCR. At the dilution point at which amplification products were unable to be detected, PCRs were repeated 10 times and the frequency of negative results was calculated (f(x=0)). The copy numbers of the target genes were calculated according to a Poisson distribution model: $\lambda=-\log_e(f(x=0))$, where $\lambda$=average copy number of the target gene.

PCR Conditions for Candidate CoCoMo Primer Sets for the Amplification of the BLV-LTR Touch-down PCR amplifications were carried out in a 20 µl volume of 1× buffer for rTaq DNA Polymerase (TOYOBO, Tokyo, Japan) containing 1.0 unit rTaq, 0.2 mM dNTPs, 1.0 mM $MgCl_2$, 500 nM of forward and reverse primers, and 1 µl of 1:1000 diluted BLV-LTR amplicon, which had been amplified from genomic DNA by nested PCR. PCR amplification was performed with a TGRADIENT thermocycler (Biometra, Gottingen, Germany) according to the following program: an initial denaturation at 95° C. for 10 min, followed by 40 cycles of 15 s at 95° C., 10 s at 60° C. to 52° C. (annealing temperature was gradually decreased from 60° C. to 52° C., by 0.2° C. every three cycles) and 10 s at 72° C. Five µl of PCR products was used for 2% agarose gel electrophoresis and amplification products were detected by ethidium bromide staining.

Melting Curve Analysis for Evaluating PCR Specificity

PCR amplifications took place in a total volume of 20 µl of 1× LightCycler FastStart DNA Master SYBR Green I (Roche Diagnostics GmbH, Basel, Switzerland) containing 500 nM of each of the CoCoMo primers, 3 mM of $MgCl_2$, and 30 ng of genomic DNA. PCR amplifications were performed with a Light Cycler 2.0 (Roche Diagnostics GmbH) according to the following program: an initial denaturation at 95° C. for 10 min, followed by 75 cycles of 15 s at 95° C., 5 s at 65° C., and 9 s at 72° C. The melting process was monitored by fluorescence of the DNA-binding SYBR Green I dye for the detection of double-stranded DNA.

Detection of BLV-LTR by Nested PCR

The first PCR amplification was done using the primers BLTRF-YR (5'-TGTATGAAAGATCATGYCGRC-3' (SEQ ID NO:10) LTR 1-21) and BLTRR (5'-AATTGTTTGCCG-GTCTCTC-3' (SEQ ID NO:11) LTR 515-533). The amplifications were carried out in a total volume of 20 µl of 1× buffer for rTaq DNA Polymerase (TOYOBO) containing 250 nM of BLTRF-YR primer and BLTRR primer, 0.5 units of rTaq polymerase, 0.2 mM dNTPs, 2.5 mM MgCl2, and 30 ng of template DNA. PCR amplification was performed with a TGRADIENT thermocycler (Biometra) according to the following program: an initial denaturation at 94° C. for 2 min, followed by 35 cycles of 30 s at 94° C., 30 s at 58° C. and 30 s at 72° C., and a final cycle of 5 min at 72° C.

The second set of PCR amplifications was performed in a total volume of 20 µl of 1× buffer for rTaq DNA Polymerase (TOYOBO) containing 250 nM of 256 primer and 453 primer (see below), 0.5 units of rTaq polymerase, 0.2 mM of dNTPs, 2.5 mM of MgCl2, and 1 µl of first-round PCR product. The oligonucleotide sequences used in the second PCR were 256 (5'-GAGCTCTCTTGCTCCCGAGAC-3' (SEQ ID NO:12), LTR 256-276) and 453 (5'-GAAACAAACGCGGGTGCAAGCCAG-3' (SEQ ID NO:13), LTR 429-453), and have been described previously [Non-Patent Literature 23]. PCR amplification was performed with a TGRADIENT thermocycler (Biometra) according to the following program: an initial denaturation at 94° C. for 2 min, followed by 35 cycles of 30 s at 94° C., 30 s at 58° C. and 30 s at 72° C., and a final cycle of 5 min at 72° C. Five µl of PCR products was used for 2% agarose gel electrophoresis and the PCR products were detected by ethidium bromide staining.

Amplification, Cloning, and DNA Sequencing of BLV-LTR Regions.

To analysis the nucleotide sequence of samples that were positive by BLV-CoCoMo-qPCR but negative by nested-PCR, genomic DNA from BLV-infected cattle was subjected to amplification by PCR using MightyAmp DNA polymerase Ver.2 (TAKARA), KOD plus Neo (TOYOBO), and TaqMan Universal Master Mix II system (AB). BLV-LTR specific oligonucleotide primers BLTR56F (5'-AACGTCA-GCTGCCAGAAA-3' (SEQ ID NO:14)), BLTR134F (5'-AAAATCCACACCCTGAGCTG-3' (SEQ ID NO:15)), CoCoMo6, CoCoMo81, and BLTR544R (5'-ACCGAGC-CCCCAATTGTTT-3' (SEQ ID NO:16)) were designed by reference to the LTR regions of BLV proviral sequences. The PCR products were subcloned into pGEM-T Easy vector (Promega) by TA cloning and the nucleotide sequence was determined by cycle sequencing using standard procedures.

Syncytium Formation Assay

The assay was performed according to a previously described procedure [Non-Patent Literatures 15, 22]. CC81 cells were grown for 72 h in a 6-cm-diameter dish and incubated with $1\times10^5$ BLV-infected PBMC in RPMI 1640 medium. Cells were fixed in May-Grunwald solution for 10 min and stained with Giemsa solution for 10 min. After washing with water, cells were examined under a light microscope. Cells containing more than five nuclei were counted as syncytia.

Statistical Analysis

Statistical analysis was conducted using R 2.10.1 statistical computing software. For multiple testing, pairwise t test was used for calculating pairwise comparisons between group levels with corrections. P-values of less than 0.05 were considered significant. Regression analysis was used to examine the correlation between the serial dilution method and the BLV-CoCoMo-qPCR method, and between the syncytium count and the provirus copy number.

TABLE 1

Primer sequences for amplification of BLV LTR candidate regions by the Coordination of Common Motif (CoCoMo) algorithm

| Primer | | | Primer annealing position in the BLV-LTR sequence[i] | |
|---|---|---|---|---|
| | ID | Sequence | 3'LTR | 5'LTR |
| (SEQ ID NO: 17) | 1 | ACCTGYYGWKAAAYTAATAMAATGC | 162-186 | 8351-8375 |
| (SEQ ID NO: 18) | 2 | CYDKYSRGYTARCGGCRCCAGAAGC | 192-216 | 8381-8405 |
| (SEQ ID NO: 19) | 3 | GSCCYDKYSRGYTARCGGCRCCAGA | 189-213 | 8378-8402 |

TABLE 1-continued

Primer sequences for amplification of BLV LTR candidate regions by the Coordination of Common Motif (CoCoMo) algorithm

| | Primer ID | Sequence | Primer annealing position in the BLV-LTR sequence[1] 3'LTR | 5'LTR |
|---|---|---|---|---|
| (SEQ ID NO: 20) | 4 | VRRAAWHYMMNMYCYKDAGCTGCTG | 132-156 | 8321-8345 |
| (SEQ ID NO: 21) | 5 | KDDWAAHTWAWWMAAWKSCGGCCCT | 169-193 | 8358-8382 |
| (SEQ ID NO: 1) | 6 | MNMYCYKDRSYKSYKSAYYTCACCT | 141-165 | 8330-8354 |
| (SEQ ID NO: 22) | 7 | YYSVRRAAWHYMMNMYCYKDAGCTG | 129-153 | 8318-8342 |
| (SEQ ID NO: 23) | 8 | GCTCCCGAGRCCTTCTGGTCGGCTA | 266-290 | 8455-8479 |
| (SEQ ID NO: 24) | 12 | NMYCYKDRSYKSYKSAYYTCACCTG | 142-166 | 8331-8355 |
| (SEQ ID NO: 25) | 17 | SGKYCYGAGYYYKCTTGCTCCCGAG | 250-274 | 8439-8463 |
| (SEQ ID NO: 26) | 20 | YSGKYCYGAGYYYKCTTGCTCCCGA | 249-273 | 8438-8462 |
| (SEQ ID NO: 27) | 22 | HVVRRWMHHYMMNMYSHKNWGCTGC | 130-154 | 8319-8343 |
| (SEQ ID NO: 28) | 30 | YYYSGKYCYGAGYYYKCTTGCTCCC | 247-271 | 8436-8460 |
| (SEQ ID NO: 29) | 32 | SGSMVCMRRARSBRYTCTYYTCCTG | 204-228 | 8393-8417 |
| (SEQ ID NO: 30) | 33 | YYYYSGKYCYGAGYYYKCTTGCTCC | 246-270 | 8435-8459 |
| (SEQ ID NO: 31) | 34 | VCMRRARSBRYTCTYYTCCTGAGAC | 208-232 | 8397-8421 |
| (SEQ ID NO: 32) | 39 | GSMVCMRRARSBRYTCTYYTCCTGA | 205-229 | 8394-8418 |
| (SEQ ID NO: 33) | 56 | MNMYMYDNVSYKVBBBRYYKCACCT | 141-165 | 8330-8354 |
| (SEQ ID NO: 34) | 58 | YSBRRGBYBKYTYKCDSCNGAGACC | 253-277 | 8442-8466 |
| (SEQ ID NO: 35) | 62 | BYSBRRGBYBKYTYKCDSCNGAGAC | 323-347 | 8441-8465 |
| (SEQ ID NO: 36) | 63 | YYYYBGBYYYSWGHYYBCKYGCTCC | 246-270 | 8587-8611 |
| (SEQ ID NO: 37) | 64 | VRDNYHHNHYYYBNRKYYBYTGACC | 354-378 | 8324-8348 |
| (SEQ ID NO: 38) | 65 | HVVNVHVNHHVVNVNSNKNWGMYGS | 43-67,<br>68-92,<br>130-154 | 8232-56,<br>8257-81,<br>8319-43 |
| (SEQ ID NO: 39) | 66 | NNHHDHBHRWDMMAHNSMBDSMSYK | 124-148,<br>169-193,<br>170-194 | 8313-37,<br>8358-82,<br>8359-83 |
| (SEQ ID NO: 40) | 68 | BNNVBBHVNVHNYYYBNYHVMYBHS | 26-50,<br>91-115,<br>247-271 | 8215-39,<br>8280-8304,<br>8436-60 |
| (SEQ ID NO: 41) | 69 | NVMNBNNHHVDNHWMHYSMBRMSCT | 123-147,<br>128-152,<br>211-235 | 8312-36,<br>8317-41,<br>8400-24 |
| (SEQ ID NO: 42) | 70 | NNNBBHVBVNNHNBBRHYYBTCTCC | 202-226,<br>360-384,<br>375-399 | 8391-8415,<br>8549-73,<br>8564-88 |
| (SEQ ID NO: 43) | 73 | TGGTCTCHGCYGAGARCCNCCCTCC | 325-349 | 8514-8538 |
| (SEQ ID NO: 44) | 76 | GCCGACCAGAAGGYCTCGGGAGCAA | 264-288 | 8453-8477 |
| (SEQ ID NO: 45) | 80 | SSSRKKBVVRVSCMRRMSSCCTTGG | 421-445 | 8610-8634 |
| (SEQ ID NO: 2) | 81 | TACCTGMCSSCTKSCGGATAGCCGA | 284-308 | 8473-8497 |
| (SEQ ID NO: 46) | 83 | KKBVVRVSCMRRMSSCCTTGGAGCG | 417-441 | 8606-8630 |
| (SEQ ID NO: 47) | 85 | GMCSSCTKSCGGATAGCCGACCAGA | 279-303 | 8468-8492 |
| (SEQ ID NO: 48) | 90 | CCTGMCSSCTKSCGGATAGCCGACC | 282-306 | 8471-8495 |

TABLE 1-continued

Primer sequences for amplification of BLV LTR candidate regions by the Coordination of Common Motif (CoCoMo) algorithm

| Primer ID | | Sequence | Primer annealing position in the BLV-LTR sequence[1] | |
|---|---|---|---|---|
| | | | 3'LTR | 5'LTR |
| (SEQ ID NO: 49) | 95 | YYYMMVMVBBKKNBTDKCCTTACCT | 304-328 | 8493-8517 |
| (SEQ ID NO: 50) | 97 | RMVVRDVBVVGVBDSMVRSCCWKRS | 421-445, 429-453 | 8610-8634, 8618-8642 |
| (SEQ ID NO: 51) | 103 | VMVVVDRVNVSSVDKVMRVSCYWGR | 421-445, 430-454 | 8610-8634, 8619-8643 |
| (SEQ ID NO: 52) | 108 | YYMMVMVBBKKNBTDKCCTTACCTG | 303-327 | 8492-8516, |
| (SEQ ID NO: 53) | 112 | VVVRRNBSVRRBBVVRVSCCMKWSG | 421-445, 428-452 | 8610-8634, 8617-8641 |
| (SEQ ID NO: 54) | 130 | NKNVVRVSCVVVVVVVSWKRGAGCG | 417-441, 484-508 | 8606-8630, 8673-8697 |
| (SEQ ID NO: 55) | 135 | NNVVNDRVNVBNNDKNNNNNBHNND | 4-28, 90-114, 105-129, etc | 8610-8634, 8619-8643, etc |
| (SEQ ID NO: 56) | 136 | BHYYYBNSSSVHKVSRGRKMGCCGA | 284-308, 495-519 | 8473-8497, 8684-8708 |
| (SEQ ID NO: 57) | 137 | DRRRSYHVSVRDRSTCDSDRCCGAG | 247-271, 336-360 | 8436-8460, 8525-8549 |
| (SEQ ID NO: 58) | 138 | WWVVDSHYSSVKKSSKSWYWGCCGA | 284-308, 337-861 | 8473-8497, 8526-8550 |
| (SEQ ID NO: 59) | 140 | NHNNNBBBSSVVTRGWSKSHGCCGA | 337-361, 495-519 | 8526-8550, 8684-8708 |
| (SEQ ID NO: 60) | 141 | NRRRVBHVVVRDRSYYNSDRCCGAG | 247-271, 336-360 | 8436-8460, 8525-8549 |
| (SEQ ID NO: 61) | 142 | NHNNNBBBSSVNYDSWSBBNGCCGA | 337-361, 495-519 | 8526-8550, 8684-8708 |
| (SEQ ID NO: 62) | 143 | VMVVVNDNNVSSVDDVMVVVCYWGR | 279-303, 421-445, 430-454 | 8468-8492, 8610-34, 8619-43 |
| (SEQ ID NO: 63) | 144 | VVVRRNNVVRDBBVVVVBSSMKWSG | 378-402, 421-445, 428-452 | 8567-8591, 8610-34, 8617-41 |

[1]Numbers indicate the position in the nucleotide sequence of the FLK-BLV subclone pBLV913 [DDBJ: EF600696].

TABLE 2

Intra- and inter-assay reproducibility of BLV-CoCoMo-qPCR

| | Proviral load[1] | | | Intra-assay[2] | | | Inter-assay[3] |
|---|---|---|---|---|---|---|---|
| No. | Exp. 1 | Exp 2 | Exp 3 | Exp. 1 | Exp. 2 | Exp. 3 | Exp. 1~3 |
| Ns105 | 1998 ± 385 | 2107 ± 296 | 1581 ± 150 | 17.9 | 14.1 | 9.5 | 14.6 |
| Ns209 | 3951 ± 691 | 3751 ± 529 | 3049 ± 150 | 17.5 | 14.1 | 4.9 | 13.2 |
| Ns126 | 20388 ± 222 | 23484 ± 1854 | 28375 ± 1381 | 1.1 | 7.9 | 4.9 | 16.7 |
| Ns226 | 30155 ± 6184 | 27247 ± 1454 | 34954 ± 3021 | 20.5 | 5.3 | 8.6 | 12.6 |
| Ns120 | 57236 ± 6127 | 59375 ± 3195 | 53225 ± 2514 | 10.7 | 5.4 | 4.7 | 5.5 |
| Ns107 | 90947 ± 0 | 73002 ± 3228 | 61388 ± 4779 | 0.0 | 4.4 | 7.8 | 19.8 |
| Ns112 | 87377 ± 7434 | 94934 ± 5891 | 84667 ± 5763 | 8.5 | 6.2 | 6.8 | 6.0 |

[1]Values represent the mean ± standard deviation (SD) of BLV proviral copy numbers in $10^5$ cells from triplicate PCR amplifications from each sample.
[2]Intra-CV: Coefficient of variation between each sample.
[3]Inter-CV: Coefficient of variation between each experiment.

TABLE 3

Comparison of BLV detection by BLV-CoCoMo-qPCR and nested PCR in cattle from Japan, Peru, Bolivia, Chile and the U.S.A.

| Country | | +/+[1] n[2] | % | −/− n | % | +/− n | % | −/+ n | % | Total number |
|---|---|---|---|---|---|---|---|---|---|---|
| Japan | A | 50 | 92.6 | 2 | 3.7 | 2 | 3.7 | 0 | 0 | 54 |
| Peru | A | 7 | 77.8 | 2 | 22.2 | 0 | 0 | 0 | 0 | 9 |
| | B | 0 | 0 | 5 | 83.3 | 1 | 16.7 | 0 | 0 | 6 |
| Bolivia | A | 2 | 40.0 | 2 | 40.0 | 1 | 20.0 | 0 | 0 | 5 |
| | B | 4 | 66.7 | 2 | 33.3 | 0 | 0 | 0 | 0 | 6 |
| | C | 5 | 35.7 | 8 | 57.1 | 1 | 7.1 | 0 | 0 | 14 |
| | D | 16 | 45.7 | 16 | 45.7 | 3 | 8.6 | 0 | 0 | 35 |
| Chile | A | 11 | 68.8 | 4 | 25.0 | 1 | 6.2 | 0 | 0 | 16 |
| | B | 0 | 0 | 6 | 100.0 | 0 | 0 | 0 | 0 | 6 |
| | C | 7 | 70.0 | 3 | 30.0 | 0 | 0 | 0 | 0 | 10 |
| USA | A | 5 | 100.0 | 0 | 0 | 0 | 0 | 0 | 0 | 5 |

[1]+, positive for detection of BLV; −, negative for detection of BLV.
[2]n, number of samples with identical decisions based on two methods.

The present invention is not limited to the description of the embodiments and examples above, but may be altered by a skilled person within the scope of the claims. An embodiment based on a proper combination of technical means disclosed in different embodiments is encompassed in the technical scope of the present invention.

INDUSTRIAL APPLICABILITY

The present invention provides: a kit for detecting bovine leukemia virus (BLV); and use thereof.

[Sequence Listing]
RK23208PCT Sequence Listing

The invention claimed is:

1. A kit for detecting Bovine leukemia virus (BLV), comprising:
   a first PCR primer including successive 20 bases or more in the base sequence denoted by SEQ ID NO: 1, the first PCR primer being oligonucleotide having 50 bases or less; and
   a second PCR primer including successive 20 bases or more in the base sequence denoted by SEQ ID NO: 2, the second PCR primer being oligonucleotide having 50 bases or less, and the second PCR primer being a degenerate primer which is a mixture of all the possible primers.

2. The kit for detecting Bovine leukemia virus (BLV), according to claim 1, wherein the first PCR primer includes successive 20 bases or more and 25 bases or less in the base sequence denoted by the SEQ ID NO: 1, the first PCR primer being oligonucleotide having 40 bases or less, and the second PCR primer includes successive 20 bases or more and 25 bases or less in the base sequence denoted by the SEQ ID NO: 2, the second PCR primer being oligonucleotide having 40 bases or less.

3. The kit for detecting Bovine leukemia virus (BLV), according to claim 1, wherein
   the first PCR primer includes the whole 25 successive bases denoted by SEQ ID NO: 1, and
   the second PCR primer includes the whole 25 successive bases denoted by SEQ ID NO: 2.

4. The kit for detecting Bovine leukemia virus (BLV), according to claim 1, wherein:
   the first PCR primer and the second PCR primer are both degenerate primers.

5. The kit for detecting Bovine leukemia virus (BLV), according to claim 1, further comprising:
   a TaqMan probe that specifically hybridizes with a gene fragment amplified by the first PCR primer and the second PCR primer.

6. The kit for detecting Bovine leukemia virus (BLV), according to claim 5, wherein the TaqMan probe includes one of the base sequences denoted by SEQ ID NOs: 3 and 4.

7. A method for detecting Bovine leukemia virus (BLV), comprising: an amplifying step of amplifying a gene fragment derived from BLV in a test sample with use of a kit for detecting BLV, the test sample having been obtained from cattle,
the kit including:
 a first PCR primer including successive 20 bases or more in the base sequence denoted by SEQ ID NO: 1, the first PCR primer being oligonucleotide having 50 bases or less; and
 a second PCR primer being a degenerate primer, which is a mixture of all the possible primers including successive 20 bases or more in the base sequence denoted by SEQ ID NO: 2, the second PCR primer being oligonucleotide having 50 bases or less.

8. The method for detecting Bovine leukemia virus (BLV), according to claim 7, wherein
 the first PCR primer includes successive 20 bases or more and 25 bases or less in the base sequence denoted by the SEQ ID NO: 1, the first primer being oligonucleotide having 40 bases or less, and
 the second PCR primer includes successive 20 bases or more and 25 bases or less in the base sequence denoted by the SEQ ID NO: 2, the second PCR primer being oligonucleotide having 40 bases or less.

9. The method for detecting Bovine leukemia virus (BLV), according to claim 7, wherein
 the first PCR primer includes the whole 25 successive bases denoted by SEQ ID NO: 1, and
 the second PCR primer includes the whole 25 successive bases denoted by SEQ ID NO: 2.

* * * * *